US012662528B2

(12) United States Patent
Combaluzier et al.

(10) Patent No.: US 12,662,528 B2
(45) Date of Patent: Jun. 23, 2026

(54) ANTI-Nogo-A ANTIBODIES AND METHODS OF MAKING AND USING THEREOF

(71) Applicant: NovaGo Therapeutics AG, Schlieren (CH)

(72) Inventors: Benoit Combaluzier, Schlieren (CH); Eduardo Paulo Morawski Vianna, Lörrach (DE); Michael Andreas Maurer, Schlieren (CH)

(73) Assignee: NovaGo Therapeutics AG, Schlieren (CH)

( * ) Notice: Subject to any disclaimer, the term of this patent is extended or adjusted under 35 U.S.C. 154(b) by 1080 days.

(21) Appl. No.: 17/770,772

(22) PCT Filed: Oct. 26, 2020

(86) PCT No.: PCT/EP2020/080076
§ 371 (c)(1),
(2) Date: Apr. 21, 2022

(87) PCT Pub. No.: WO2021/079002
PCT Pub. Date: Apr. 29, 2021

(65) Prior Publication Data
US 2023/0399390 A1 Dec. 14, 2023

(30) Foreign Application Priority Data

Oct. 24, 2019 (EP) ..................................... 19205006

(51) Int. Cl.
| | |
|---|---|
| *A61K 39/395* | (2006.01) |
| *A61K 39/00* | (2006.01) |
| *A61K 49/00* | (2006.01) |
| *A61P 25/00* | (2006.01) |
| *A61P 25/28* | (2006.01) |
| *C07K 16/00* | (2006.01) |
| *C07K 16/18* | (2006.01) |
| *C07K 16/22* | (2006.01) |
| *G01N 33/53* | (2006.01) |
| *G01N 33/68* | (2006.01) |

(52) U.S. Cl.
CPC .............. *C07K 16/22* (2013.01); *A61K 39/00* (2013.01); *A61K 39/0007* (2013.01); *A61K 39/395* (2013.01); *A61K 39/39533* (2013.01); *A61P 25/00* (2018.01); *A61P 25/28* (2018.01); *C07K 16/00* (2013.01); *C07K 16/18* (2013.01); *G01N 33/6896* (2013.01); *A61K 2039/505* (2013.01); *C07K 2317/10* (2013.01); *C07K 2317/21* (2013.01); *C07K 2317/24* (2013.01); *C07K 2317/51* (2013.01); *C07K 2317/515* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/624* (2013.01); *C07K 2317/71* (2013.01); *C07K 2317/76* (2013.01); *C07K 2317/92* (2013.01); *C07K 2317/94* (2013.01)

(58) Field of Classification Search
CPC .......... C07K 2317/55; C07K 2317/565; C07K 16/18; C07K 16/22; C07K 2317/76; C07K 2317/54; C07K 2317/56; C07K 2317/622; A61K 2039/505; A61K 38/1709; A61K 38/17; A61P 25/00; A61P 25/28; A61P 25/16; A61P 25/02; A61P 27/02; A61P 21/00
See application file for complete search history.

(56) References Cited

U.S. PATENT DOCUMENTS

| | | | | |
|---|---|---|---|---|
| 7,780,964 B2 * | 8/2010 | Ellis | ........................ | A61P 25/16 |
| | | | | 530/387.9 |
| 7,785,593 B2 * | 8/2010 | Barske | .................... | A61P 25/24 |
| | | | | 530/387.9 |
| 8,535,666 B2 * | 9/2013 | Barske | .................... | A61P 27/02 |
| | | | | 424/139.1 |
| 8,828,390 B2 * | 9/2014 | Herrera | ............. | A61K 39/0005 |
| | | | | 424/133.1 |
| 10,647,768 B2 * | 5/2020 | Johnson | ................. | C07K 16/30 |
| 10,752,695 B2 * | 8/2020 | Van De Winkel | ........ | A61P 7/00 |
| 2006/0183678 A1 * | 8/2006 | Barske | .................... | A61P 25/02 |
| | | | | 530/350 |
| 2010/0267934 A1 * | 10/2010 | Van De Winkel | ...... | A61P 15/00 |
| | | | | 435/69.6 |
| 2011/0059110 A1 * | 3/2011 | Barske | .................... | A61P 25/24 |
| | | | | 536/23.53 |
| 2011/0268729 A1 | 11/2011 | Abila et al. | | |
| 2013/0136737 A1 * | 5/2013 | Herrera | .............. | A61K 39/3955 |
| | | | | 424/133.1 |
| 2025/0161481 A1 * | 5/2025 | Lu | ...................... | A61K 38/1774 |

FOREIGN PATENT DOCUMENTS

| | | | | |
|---|---|---|---|---|
| JP | 2006-523087 | 10/2006 | | |
| JP | 2011-527317 | 10/2011 | | |
| WO | WO-2008145139 A1 * | 12/2000 | ............... | A61P 7/00 |
| WO | WO-2004052932 A2 * | 6/2004 | ............. | A61P 25/16 |
| WO | 2005/012360 A2 | 2/2005 | | |
| WO | WO 2005/061544 | 7/2005 | | |

(Continued)

OTHER PUBLICATIONS

Oertle et al., J. Neurosci. 2003;23:5393-5406.*

(Continued)

*Primary Examiner* — Chang-Yu Wang
(74) *Attorney, Agent, or Firm* — Jones Day

(57) ABSTRACT

Provided are novel human-derived monoclonal neutralizing Nogo-A specific antibodies as well as fragments, derivatives and variants thereof as well as methods related thereto. Polynucleotides, vectors, host cells and kits related to the Nogo-A specific antibodies are also provided. The antibodies, immunoglobulin chain(s), as well as binding fragments, derivatives and variants thereof can be used in pharmaceutical and diagnostic compositions for Nogo-A targeted immunotherapy and diagnosis, respectively.

18 Claims, 16 Drawing Sheets

Specification includes a Sequence Listing.

(56)           References Cited

FOREIGN PATENT DOCUMENTS

| WO | WO-2005061544 A2 * | 7/2005 | ................. A61P 9/00 |
| WO | WO 2007/068750 | 6/2007 | |
| WO | 2008/081008 A1 | 7/2008 | |
| WO | WO-2008145142 A1 * | 12/2008 | .............. A61P 37/06 |
| WO | WO 2009/056509 | 5/2009 | |
| WO | WO 2010/004031 | 1/2010 | |
| WO | WO-2012004773 A1 * | 1/2012 | ......... A61K 39/3955 |
| WO | 2018/160993 A1 | 9/2018 | |

OTHER PUBLICATIONS

MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Chen et al.,J. Mol. Bio., 1999; 293: 865-881.*
Wu et al.,J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
Holm et al., Mol. Immunol., 2007; 44: 1075-1084.*
Bregman, Barbara et al., "Recovery from spinal cord injury mediated by antibodies to neurite growth inhibitors," Nature, 378 (Nov. 30, 1995) 498-501.
Brown, McKay et al., "Tolerance to Single, but Not Multiple, Amino Acid Replacements in Antibody $V_H$ CDR2," The Journal of Immunology, 156 (1996) 3285-3291.
Chen, Ching et al., "Enhancement and destruction of antibody function by somatic mutation: unequal occurrence is controlled by V gene combinatorial associations," The EMBO Journal, 14:12 (1995) 2784-2794.
Chen, Maio S. et al., "Nogo-A is a myelin-associated neurite outgrowth inhibitor and an antigen for monoclonal antibody IN-1," Nature, 403 (Jan. 27, 2000) 434-439.
Colman, P.M., "Effects of amino acid sequence changes on antibody-antigen interactions," Research in Immunology, 145:1 (1994) 33-36.
Freund, Patrick et al., "Nogo-A-specific antibody treatment enhances sprouting and functional recovery after cervical lesion in adult primates," Nature Medicine, 12:7 (Jul. 2006) 790-792.
Hamadjida, Adjia et al., "Influence of anti-Nogo-A antibody treatment on the reorganization of callosal connectivity of the premotor cortical areas following unilateral lesion of primary motor cortex (M1) in adult macaque monkeys," Exp Brain Res., 223 (2012) 321-340.
Kucher, Klaus et al., "First-in-Man Intrathecal Application of Neurite Growth-Promoting Anti-Nogo-A Antibodies in Acute Spinal Cord Injury," Neurorehabilitation and Neural Repair, 32(6-7) (2018) 578-589.

Liebscher, Thomas et al., "Nogo-A Antibody Improves Regeneration and Locomotion of Spinal Cord-Injured Rats," Annals of Neurology, 58 (2005) 706-719.
Mdzomba, Julius Baya et al., "Nogo-A inactivation improves visual plasticity and recovery after retinal injury," Cell Death and Disease, 9:727 (2018) 14 pages.
Muranova, Tatyana A. et al., "Crystallization of a carbamatase catalytic antibody Fab fragment and its complex with a transition-state analogue," Acta Crystallographica Section D, Biological Crystallography, D60 (2004) 172-174.
Schmandke, Antonio et al., "Nogo-A: Multiple Roles in CNS Development, Maintenance and Disease," Neuroscientist, 20:4 (Aug. 2014) 372-386.
Schnell, Lisa et al., "Axonal regeneration in the rat spinal cord produced by an antibody against myelin-associated neurite growth inhibitors," Nature, 343 (Jan. 18, 1990) 269-272.
Thallmair, Michaela et al., "Neurite growth inhibitors restrict plasticity and functional recovery following corticospinal tract lesions," Nature Neuroscience, 1:2 (Jun. 1998) 124-131.
Wahl, A.S. et al., "Asynchronous therapy restores motor control by rewiring of the rat corticospinal tract after stroke," Science, 344:6189 (Jun. 13, 2014) 1250-1255.
Watson, Brant D. et al., "Induction of Reproducible Brain Infarction by Photochemically Initiated Thrombosis," Ann. Neurol., 17 (1985) 497-504.
Weinmann, Oliver et al., "Intrathecally infused antibodies against Nogo-A penetrate the CNS and downregulate the endogenous neurite growth inhibitor Nogo-A," Mol. Cell Neurosci., 32 (2006) 161-173.
"NISCI—Nogo Inhibition in Spinal Cord Injury (NISCI)" ClinicalTrials.gov, National Library of Medicine, Identifier: NCT03935321, Sponsor: University of Zurich (Apr. 4, 2023).
Elena Rojo Romeo (Authorized Officer), International Search Report and Written Opinion dated Jun. 11, 2021 for International Application No. PCT/EP2020/080076, 25 Pages.
Brösamle et al., "Regeneration of Lesioned Corticospinal Tract Fibers in the Adult Rat Induced by a Recombinant, Humanized IN-1 Antibody Fragment", The Journal of Neuroscience, 2000, vol. 20, No. 21, pp. 8061-8068.
Joly et al., "Nogo-A inhibits vascular regeneration in ischemic retinopathy", GLIA, 2018, vol. 66, No. 10, pp. 2079-2093.
Lindau et al., "Rewiring of the corticospinal tract in the adult rat after unilateral stroke and anti-Nogo-A therapy", Brain, 2014, vol. 137, No. 3, pp. 739-756.
Meininger et al., "Safety and efficacy of ozanezumab in patients with amyotrophic lateral sclerosis: a randomised, double-blind, placebo-controlled, phase 2 trial", Lancet Neurology, 2017, vol. 16, pp. 208-216.
Oertle et al., "Nogo-A Inhibits Neurite Outgrowth and Cell Spreading with Three Discrete Regions", The Journal of Neuroscience, 2003, vol. 23, No. 13, pp. 5393-5406.
Rudikoff et al., "Single amino acid substitution altering antigen-binding specificity", PNAS, 1982, vol. 79, pp. 1979-1983.
Rust et al., "Nogo-A targeted therapy promotes vascular repair and functional recovery following stroke", PNAS, 2019, vol. 116, No. 28, pp. 14270-14279, and Supplementary Materials and Methods.

* cited by examiner

A      NG004 (variable heavy chain sequence VH) – SEQ ID NO: 2

```
FR1-------------------------CDR1-FR2----------CDR2------------
EVQLVESGGGVVQPGRSLRLSCAASGFTFRSHAMHWVRQAPGKGLEWVAVTSYDGTNKYYADSVKG

FR3----------------------------CDR3-------FR4--------
RFTISKDNSKNTLYLQMDSLRVEDTAVYYCARGRAVAGTREDYWGQGTLVTVSS
```

NG004 (variable kappa chain sequence VL) – SEQ ID NO: 7

```
FR1--------------------CDR1------------FR2-----------CDR2---
DIQMTQSPDSLAVSLGERATINCKSSQSVLFSSNSKNYLAWYQQKPGQPPKVLIYWASTRES

FR3------------------------------CDR3-----FR4-------
GVPDRFSGSGSGTDFTLTISSLQAEDVAVYYCQQYYTTRPTFGLGTKVDIK
```

B      NG034 (variable heavy chain sequence VH)  – SEQ ID NO: 12

```
FR1--------------------------CDR1-FR2----------CDR2-------------
EVQLVETGGGLVPPGGSLRLSCAASGFTFTNYSMHWVRLAPGKRLEYISAISSDGGDPFYASSVKG

FR3-----------------------------CDR3-FR4--------
RVAISRDNSKKTLYLQMGRLRPEDTAVYYCVSDAFDVWGQGTMVTVSS
```

NG034 (variable kappa chain sequence VL)  – SEQ ID NO: 17

```
FR1--------------------CDR1-----------FR2-----------CDR2---
EIVLTQSPLSLSVTLGQPASISCRSSQSLLYSNGNTYLNWFQQRPGQSPRRLLYRVSNRDS

FR3------------------------------CDR3-----FR4-------
GVPDRFSGSGSGTHFTLKISRVEAEDVGVYYCMQGTHWPRTFGQGTKVEIK
```

Fig. 1

A
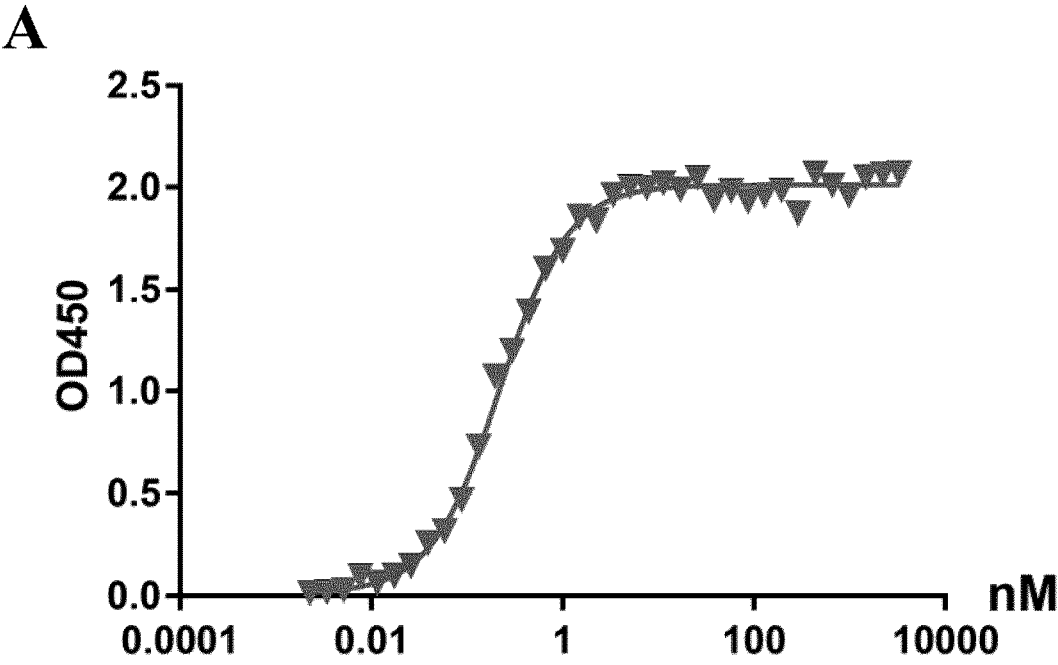
B
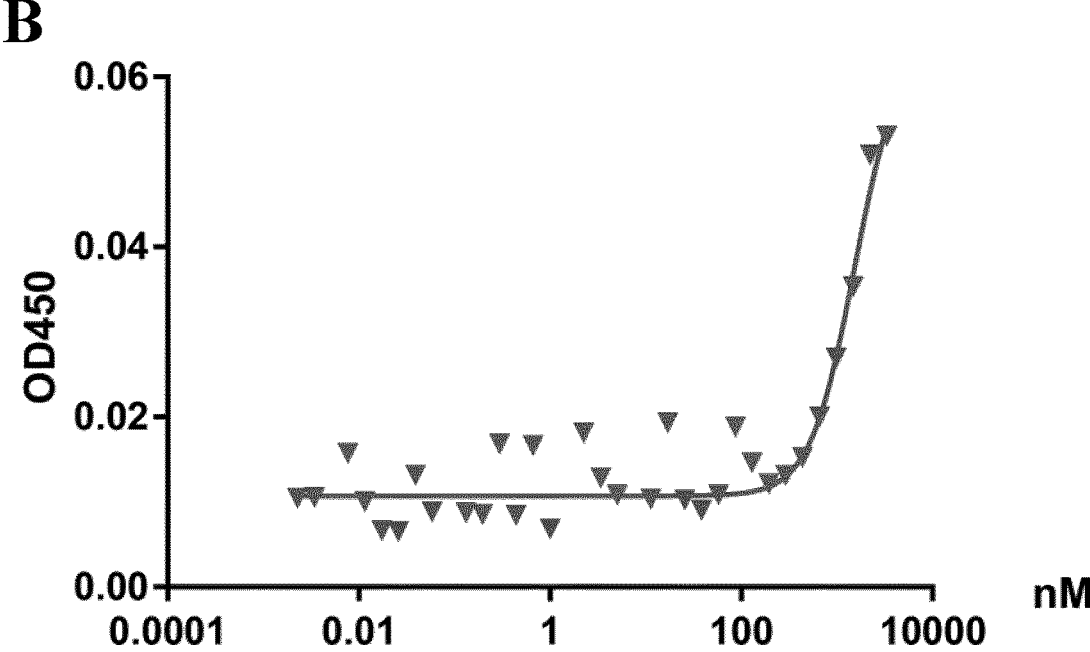
Fig. 2

C
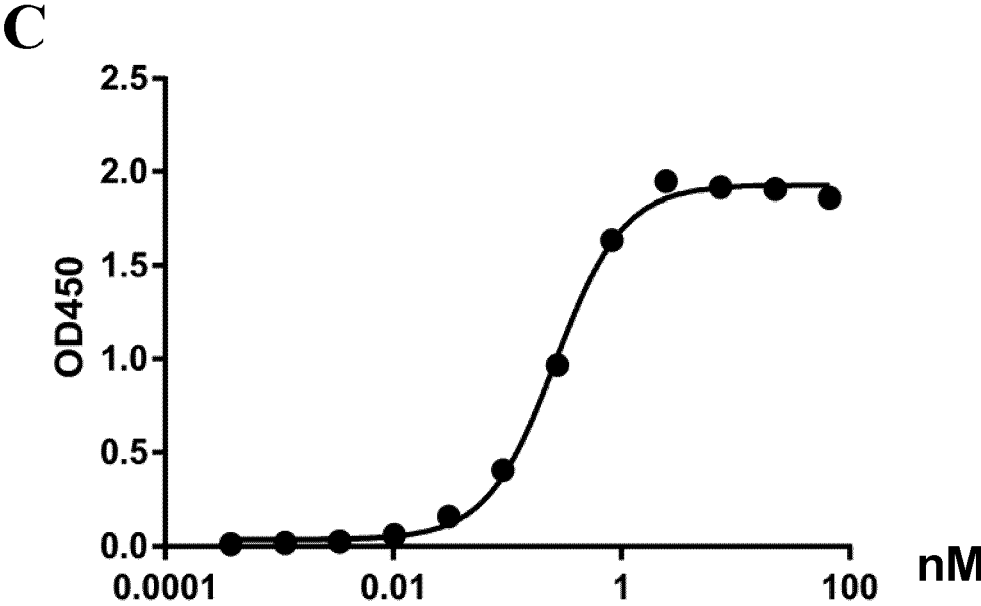
D
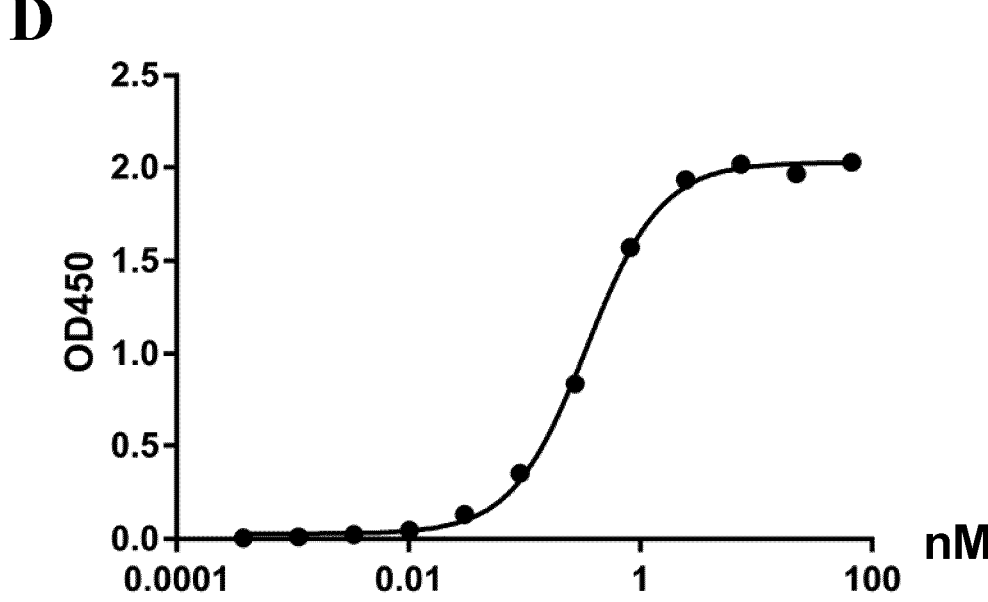
Fig. 2 (continued)

E

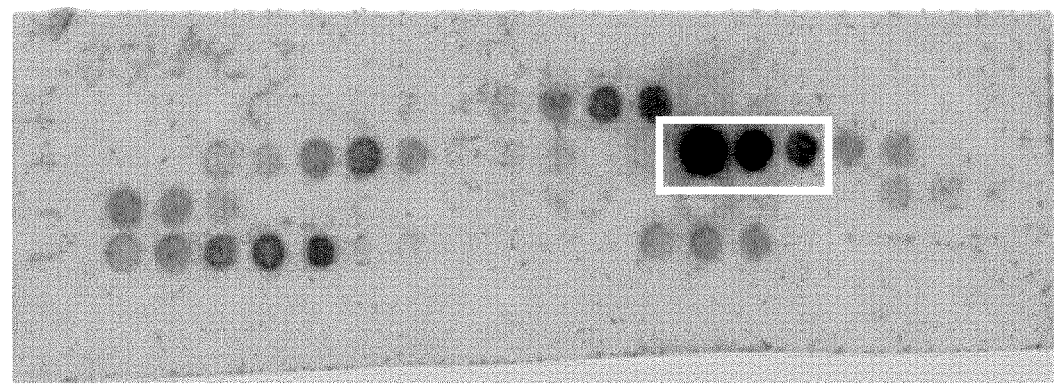
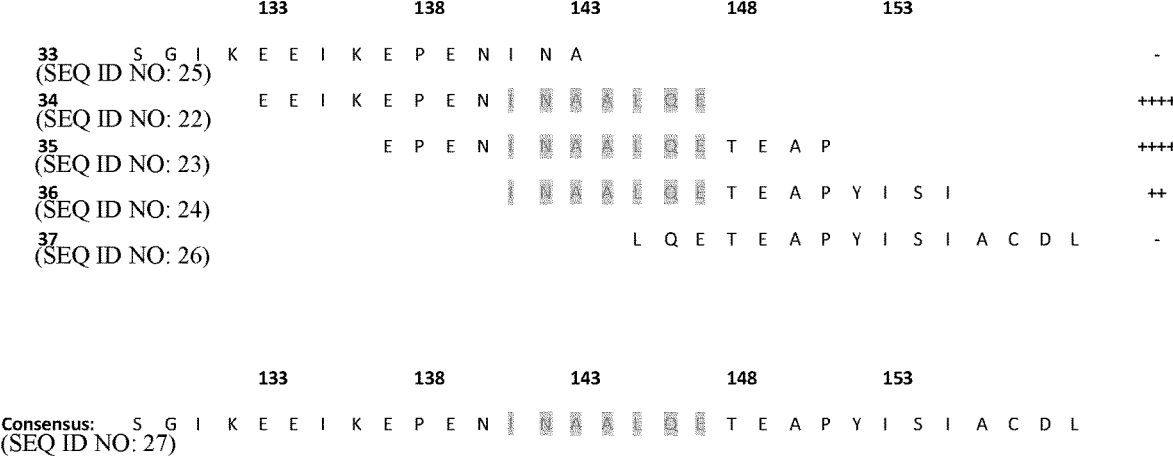
Fig. 3

A
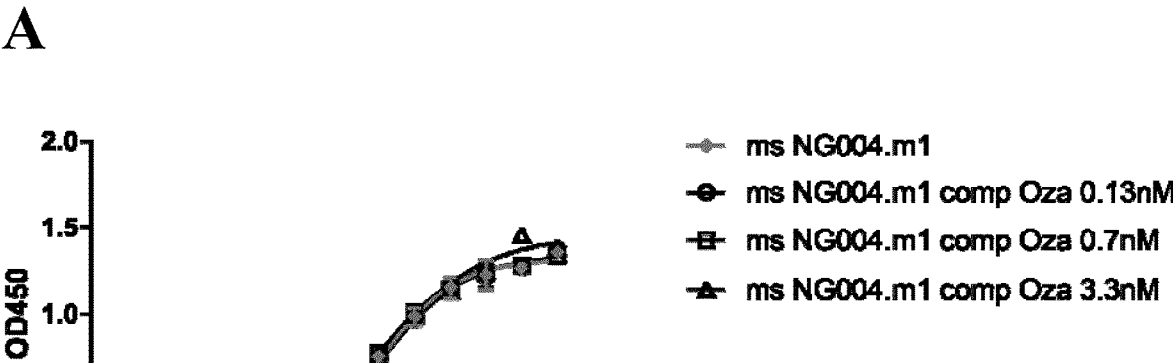
B
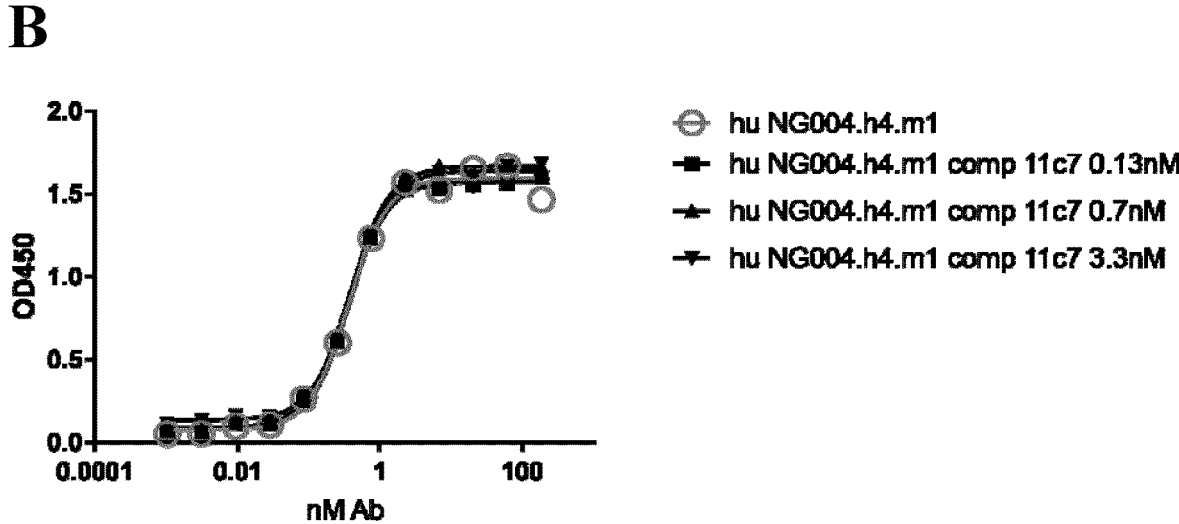
Fig. 4

C

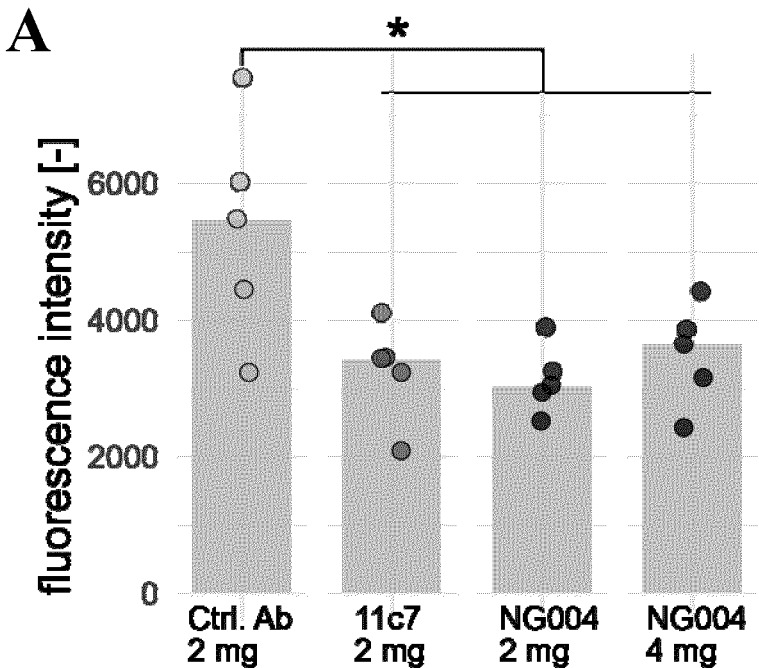
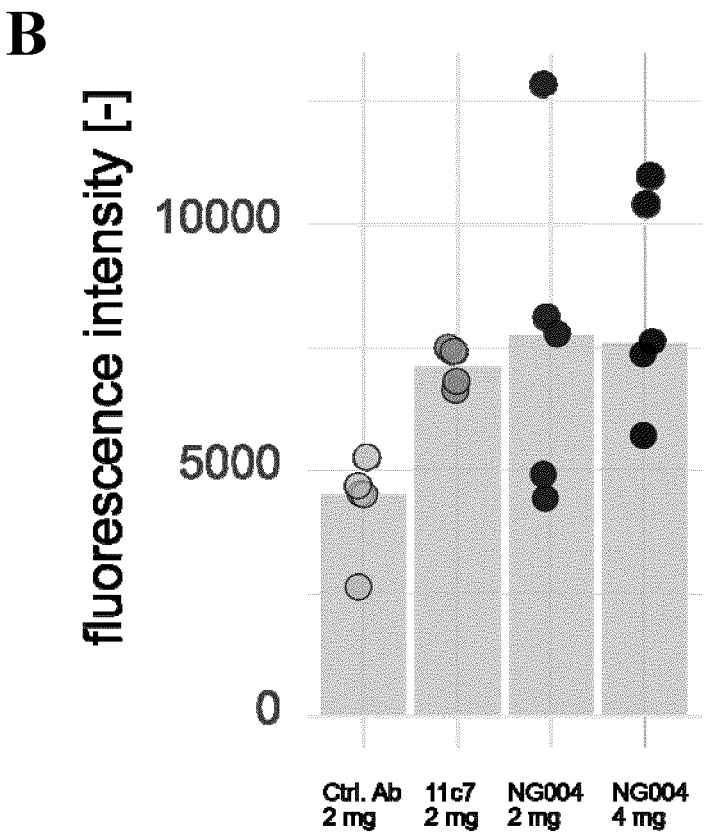
Fig. 5

C

A
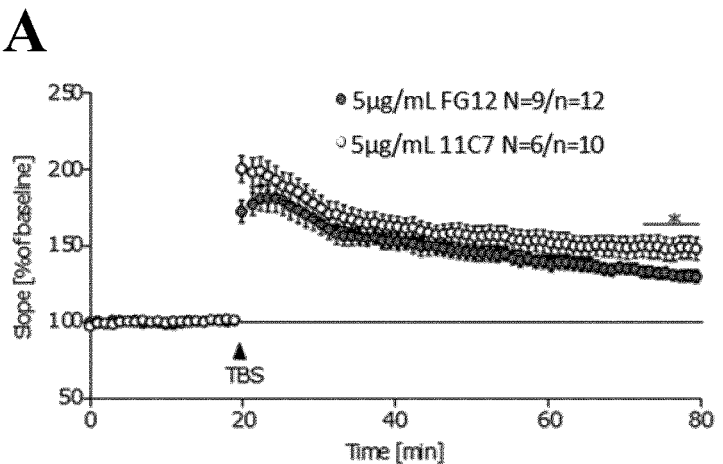
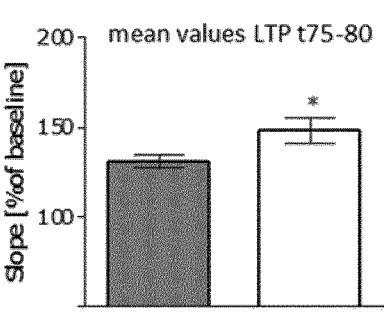
B
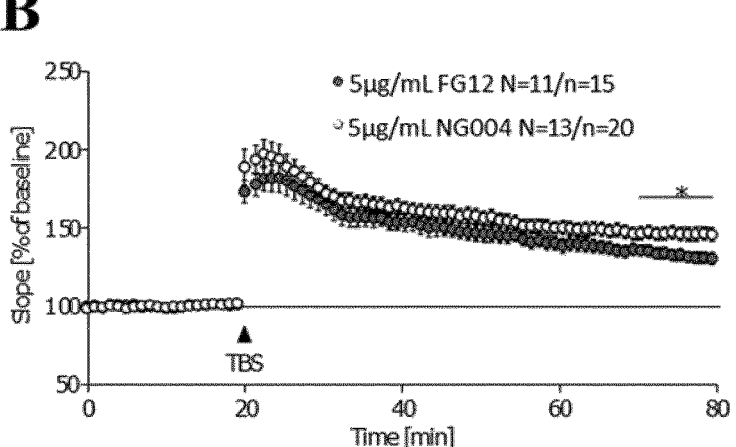
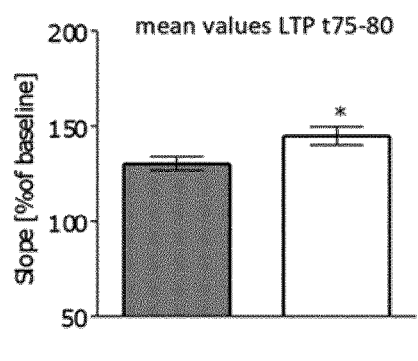
C
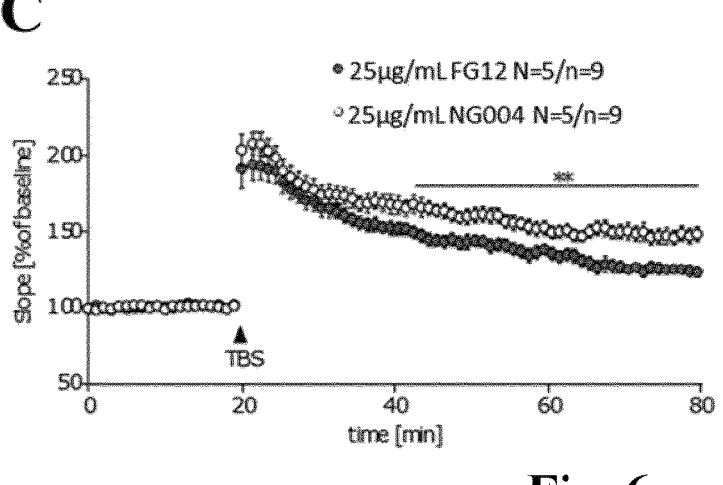
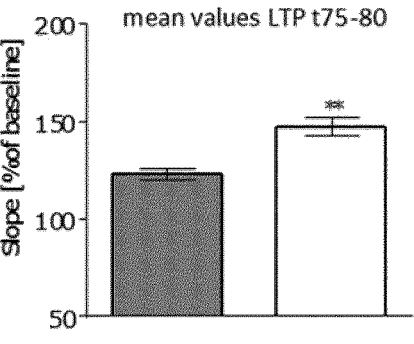
Fig. 6

A
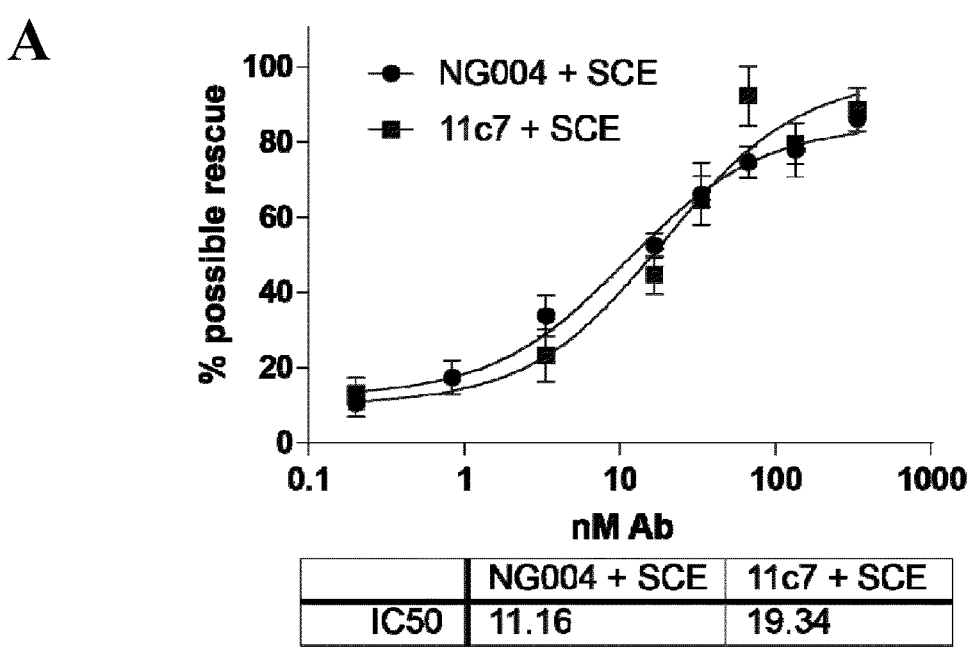
| | NG004 + SCE | 11c7 + SCE |
|---|---|---|
| IC50 | 11.16 | 19.34 |
B
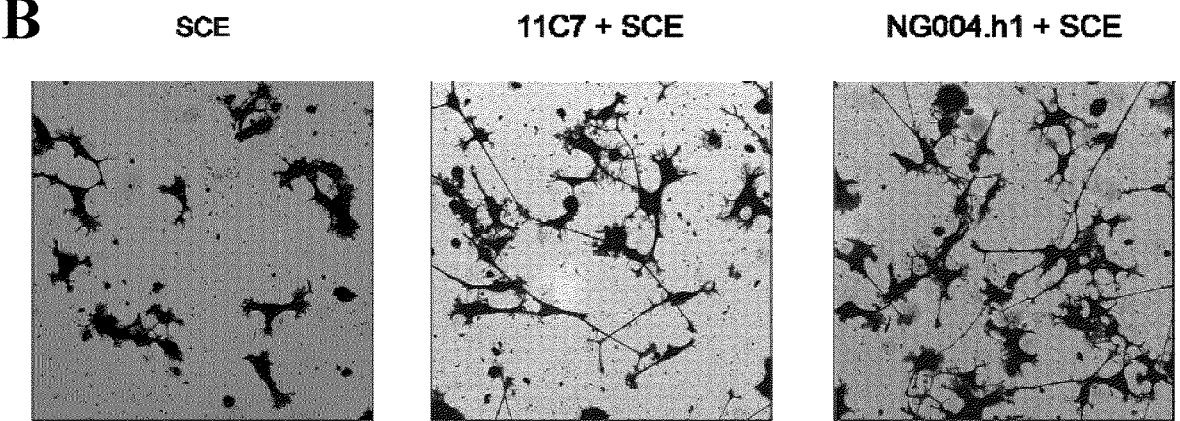
SCE         11C7 + SCE         NG004.h1 + SCE
Fig. 7

C
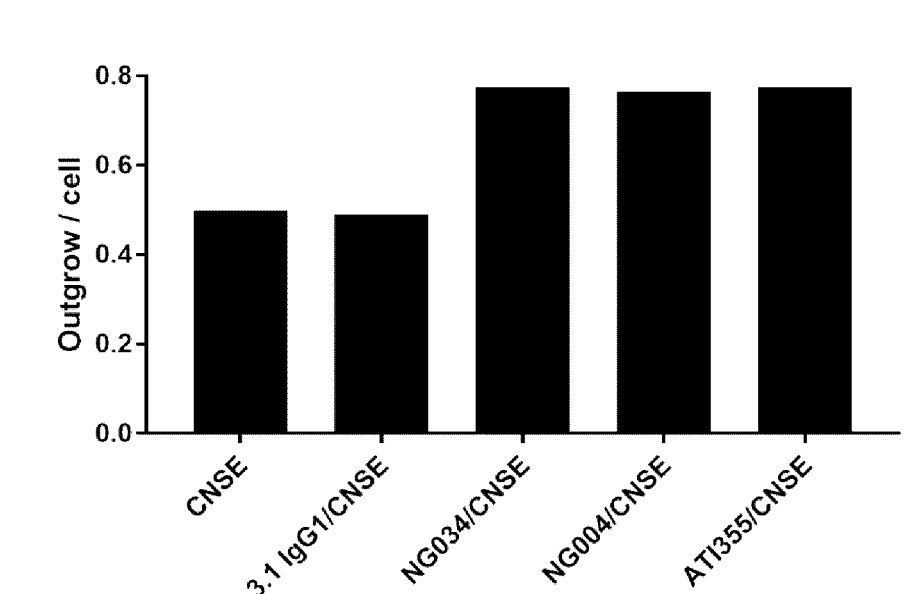
D
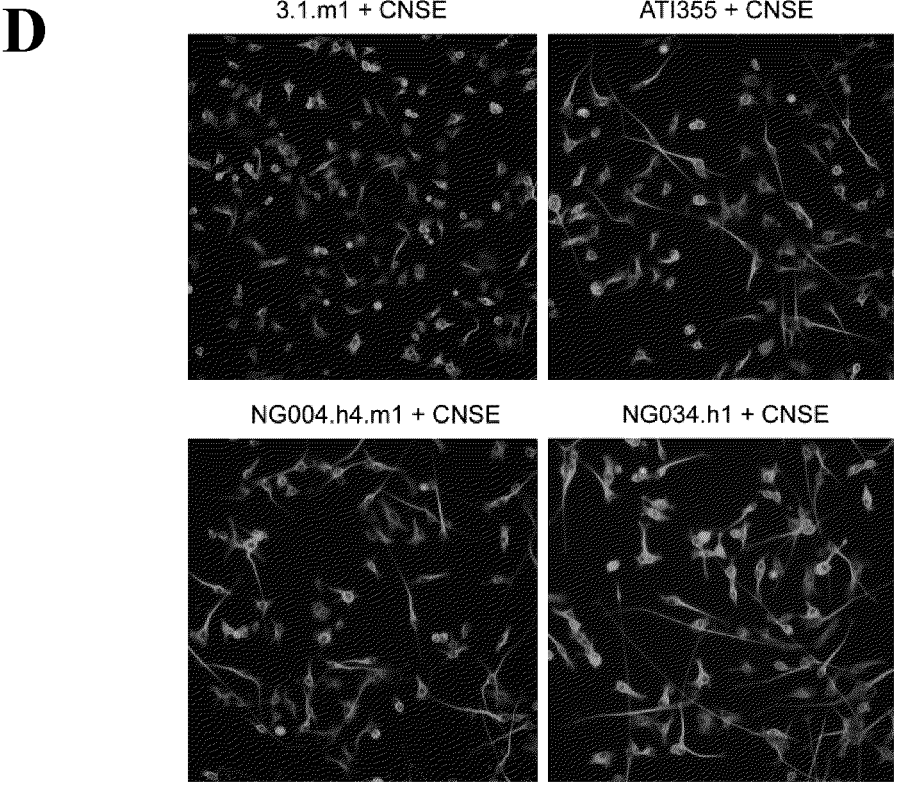
Fig. 7 (continued)

A
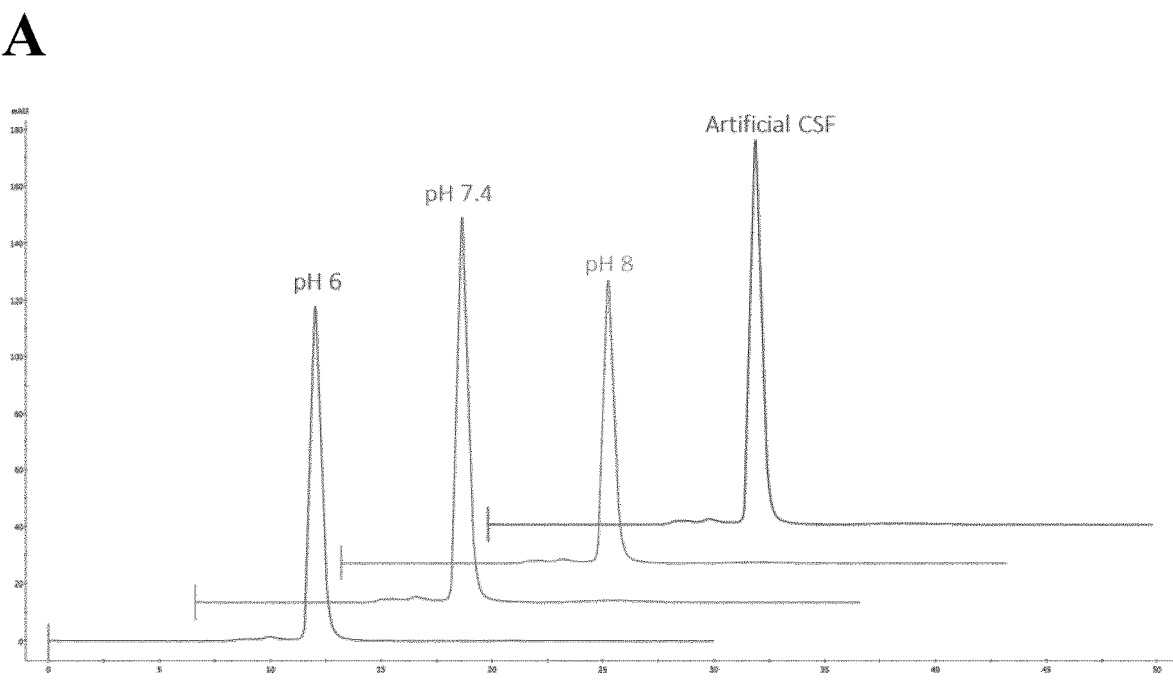
B
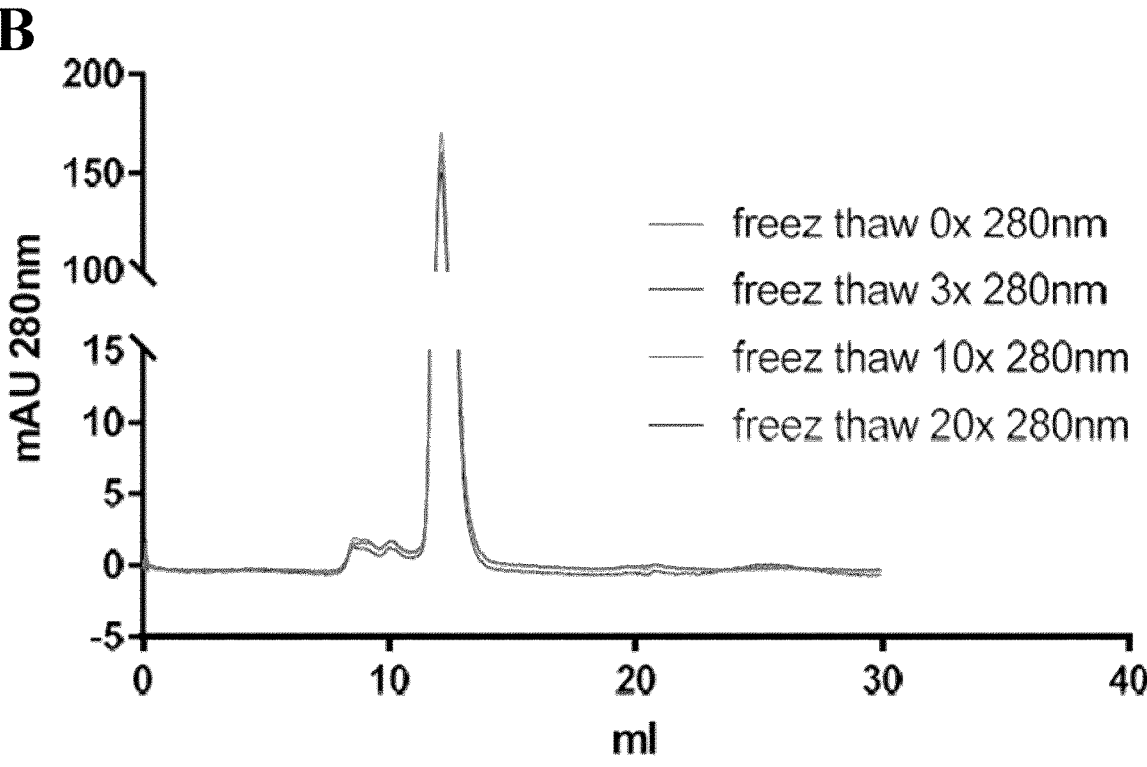
Fig. 9

A
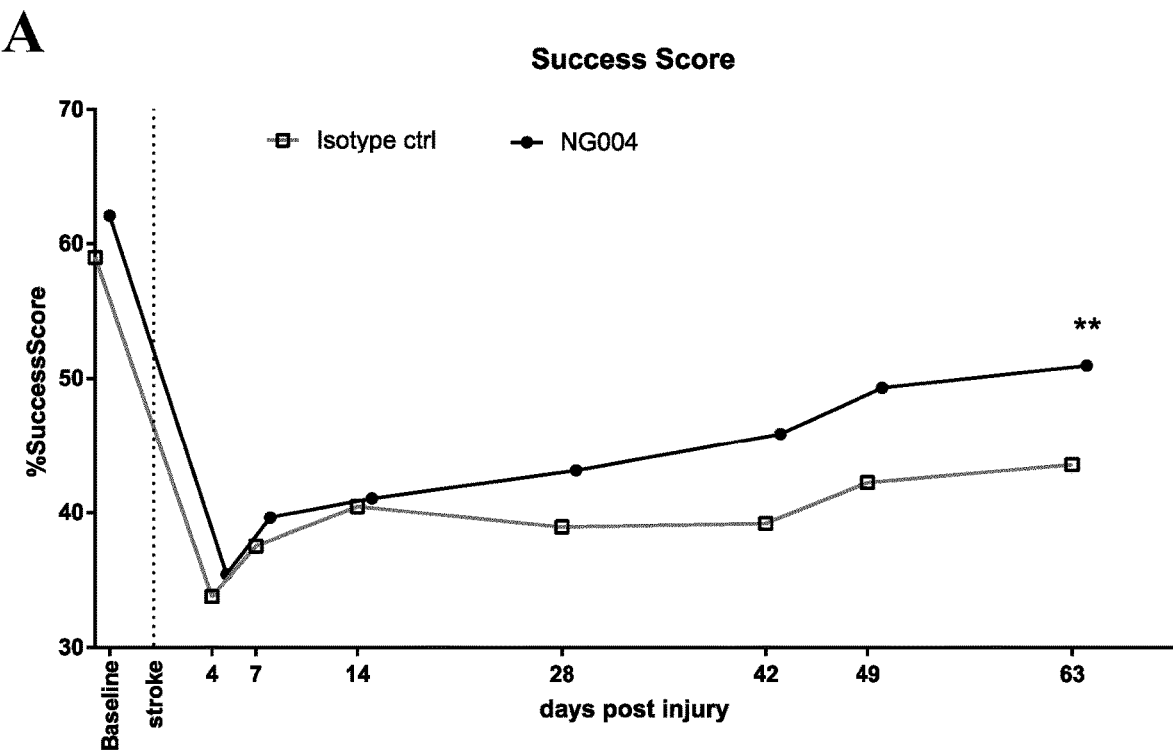
B
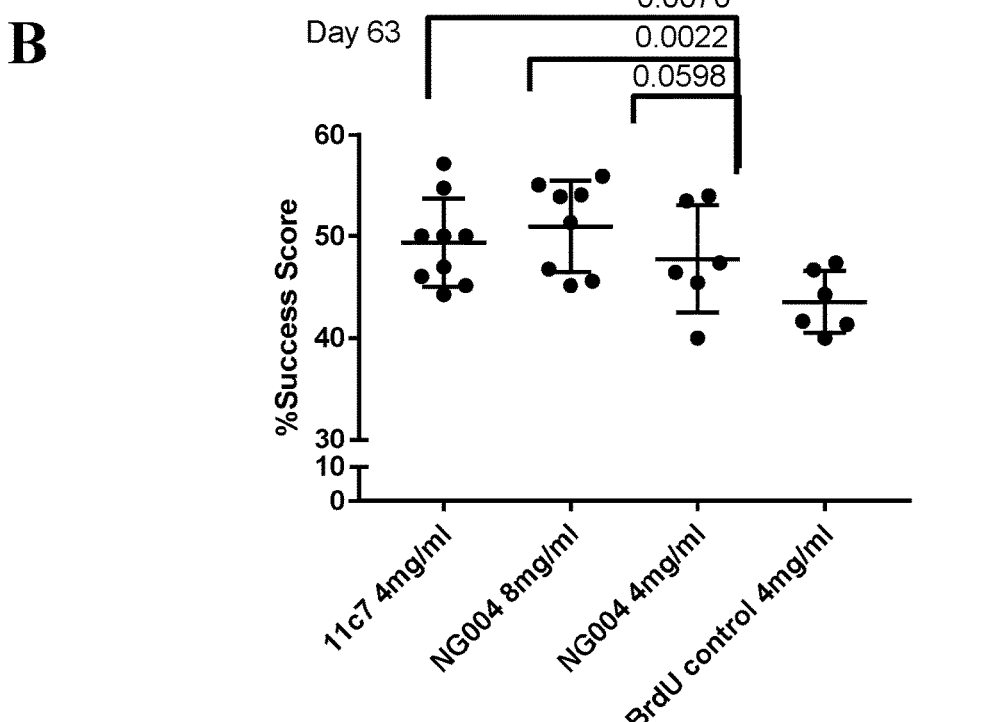
Fig. 10

SEQUENCE LISTING

<160> NUMBER OF SEQ ID NOS: 27

<210> SEQ ID NO 1
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: NG004 variable heavy chain (VH) sequence

<400> SEQUENCE: 1

```
gag gtg cag ctg gtg gag tct ggg gga ggc gtg gtc cag cct ggg agg        48
Glu Val Gln Leu Val Glu Ser Gly Gly Gly Val Val Gln Pro Gly Arg
```

```
1             5              10             15 tcc ctg aga ctc tcc tgt gca gcc tct gga ttc acc ttc agg agc cat       96
Ser Leu Arg Leu Ser Cys Ala Ala Ser Gly Phe Thr Phe Arg Ser His
        20             25             30 gct atg cac tgg gtc cgc cag gct cca ggc aag ggg ctg gag tgg gtg      144
Ala Met His Trp Val Arg Gln Ala Pro Gly Lys Gly Leu Glu Trp Val
        35             40             45 gca gtt aca tca tat gat gga acc aat aaa tac tac gca gac tcc gtg      192
Ala Val Thr Ser Tyr Asp Gly Thr Asn Lys Tyr Tyr Ala Asp Ser Val
        50             55             60 aag ggc cga ttc acc atc tcc aaa gac aat tcc aag aac acg ctg tat      240
Lys Gly Arg Phe Thr Ile Ser Lys Asp Asn Ser Lys Asn Thr Leu Tyr
65             70             75             80 ctg caa atg gac agc ctc aga gtt gag gac acg gct gtg tat tac tgt      288
Leu Gln Met Asp Ser Leu Arg Val Glu Asp Thr Ala Val Tyr Tyr Cys
               85             90             95 gcg aga ggc cga gca gtg gct ggt acg agg gaa gat tat tgg ggc cag      336
Ala Arg Gly Arg Ala Val Ala Gly Thr Arg Glu Asp Tyr Trp Gly Gln
           100            105            110 gga acc ctg gtc acc gtc tcc tcg                                      360
Gly Thr Leu Val Thr Val Ser Ser
       115            120
```

```
<210> SEQ ID NO 2
<211> LENGTH: 120
<212> TYPE: PRT
<213> ORGANISM: Homo sapiens

<400> SEQUENCE: 2

Glu Val Gln Leu Val Glu Ser Gly Gly Gly Val Val Gln Pro Gly Arg
1             5              10             15

Ser Leu Arg Leu Ser Cys Ala Ala Ser Gly Phe Thr Phe Arg Ser His
        20             25             30

Ala Met His Trp Val Arg Gln Ala Pro Gly Lys Gly Leu Glu Trp Val
        35             40             45

Ala Val Thr Ser Tyr Asp Gly Thr Asn Lys Tyr Tyr Ala Asp Ser Val
        50             55             60

Lys Gly Arg Phe Thr Ile Ser Lys Asp Asn Ser Lys Asn Thr Leu Tyr
65             70             75             80

Leu Gln Met Asp Ser Leu Arg Val Glu Asp Thr Ala Val Tyr Tyr Cys
               85             90             95

Ala Arg Gly Arg Ala Val Ala Gly Thr Arg Glu Asp Tyr Trp Gly Gln
           100            105            110

Gly Thr Leu Val Thr Val Ser Ser
       115            120
```

```
<210> SEQ ID NO 3
<211> LENGTH: 5
<212> TYPE: PRT
<213> ORGANISM: Homo sapiens

<400> SEQUENCE: 3

Ser His Ala Met His
1             5
```

```
<210> SEQ ID NO 4
<211> LENGTH: 17
<212> TYPE: PRT
<213> ORGANISM: Homo sapiens
```

<400> SEQUENCE: 4

Val Thr Ser Tyr Asp Gly Thr Asn Lys Tyr Tyr Ala Asp Ser Val Lys
1               5                   10                  15

Gly

<210> SEQ ID NO 5
<211> LENGTH: 11
<212> TYPE: PRT
<213> ORGANISM: Homo sapiens

<400> SEQUENCE: 5

Gly Arg Ala Val Ala Gly Thr Arg Glu Asp Tyr
1               5                   10

<210> SEQ ID NO 6
<211> LENGTH: 339
<212> TYPE: DNA
<213> ORGANISM: Homo sapiens
<220> FEATURE:
<221> NAME/KEY: CDS
<222> LOCATION: (1)..(339)
<223> OTHER INFORMATION: NG004 variable kappa chain (VK) sequence

<400> SEQUENCE: 6 gac atc cag atg acc cag tct cca gac tcc ctg gct gtg tct ctg ggc        48
Asp Ile Gln Met Thr Gln Ser Pro Asp Ser Leu Ala Val Ser Leu Gly
1               5                   10                  15 gag agg gcc acc atc aac tgc aag tcc agc cag agt gtt tta ttc agc        96
Glu Arg Ala Thr Ile Asn Cys Lys Ser Ser Gln Ser Val Leu Phe Ser
                20                  25                  30 tcc aac agt aag aac tac tta gct tgg tac cag cag aaa cca gga cag       144
Ser Asn Ser Lys Asn Tyr Leu Ala Trp Tyr Gln Gln Lys Pro Gly Gln
        35                  40                  45 cct cct aag gtg ctc att tac tgg gca tct acc cgg gaa tcc ggg gtc       192
Pro Pro Lys Val Leu Ile Tyr Trp Ala Ser Thr Arg Glu Ser Gly Val
    50                  55                  60 cct gac cga ttc agt ggc agc ggg tct ggg aca gat ttc act ctc acc       240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa       288
Ile Ser Ser Leu Gln Ala Glu Asp Val Ala Val Tyr Tyr Cys Gln Gln
                85                  90                  95 tat tat act act cgc cct acg ttc ggc cta ggg acc aaa gtg gat atc       336
Tyr Tyr Thr Thr Arg Pro Thr Phe Gly Leu Gly Thr Lys Val Asp Ile
                100                 105                 110 aaa                                                                    339
Lys

<210> SEQ ID NO 7
<211> LENGTH: 113
<212> TYPE: PRT
<213> ORGANISM: Homo sapiens

<400> SEQUENCE: 7

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
                20                  25                  30

Ser Asn Ser Lys Asn Tyr Leu Ala Trp Tyr Gln Gln Lys Pro Gly Gln
        35                  40                  45

Pro Pro Lys Val Leu Ile Tyr Trp Ala Ser Thr Arg Glu Ser Gly Val

```
        50              55              60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Arg Pro Thr Phe Gly Leu Gly Thr Lys Val Asp Ile
            100                 105                 110

Lys

<210> SEQ ID NO 8
<211> LENGTH: 17
<212> TYPE: PRT
<213> ORGANISM: Homo sapiens

<400> SEQUENCE: 8

Lys Ser Ser Gln Ser Val Leu Phe Ser Ser Asn Ser Lys Asn Tyr Leu
1               5                   10                  15

Ala

<210> SEQ ID NO 9
<211> LENGTH: 7
<212> TYPE: PRT
<213> ORGANISM: Homo sapiens

<400> SEQUENCE: 9

Trp Ala Ser Thr Arg Glu Ser
1               5

<210> SEQ ID NO 10
<211> LENGTH: 9
<212> TYPE: PRT
<213> ORGANISM: Homo sapiens

<400> SEQUENCE: 10

Gln Gln Tyr Tyr Thr Thr Arg Pro Thr
1               5

<210> SEQ ID NO 11
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: NG034 variable heavy chain (VH) sequence

<400> SEQUENCE: 11 gag gtg cag ctg gtg gag act ggg gga ggc ttg gtc cca ccg ggg ggg        48
Glu Val Gln Leu Val Glu Thr Gly Gly Gly Leu Val Pro Pro Gly Gly
1               5                   10                  15 tcc ctg aga ctc tcc tgt gca gcc tct gga ttc acc ttc acc aac tat       96
Ser Leu Arg Leu Ser Cys Ala Ala Ser Gly Phe Thr Phe Thr Asn Tyr
                20                  25                  30 tct atg cac tgg gtc cgc ctg gct cca ggg aag aga ctg gaa tat att      144
Ser Met His Trp Val Arg Leu Ala Pro Gly Lys Arg Leu Glu Tyr Ile
            35                  40                  45 tca gct att agt agt gat ggc ggt gac cca ttt tat gca agc tct gtg      192
Ser Ala Ile Ser Ser Asp Gly Gly Asp Pro Phe Tyr Ala Ser Ser Val
        50                  55                  60 aag ggc aga gtc gcc atc tcc aga gac aat tcc aag aag acg ttg tat      240
Lys Gly Arg Val Ala Ile Ser Arg Asp Asn Ser Lys Lys Thr Leu Tyr
65                  70                  75                  80
```

```
ctt caa atg ggc aga ctg aga cct gag gac acg gct gta tat tat tgt        288
Leu Gln Met Gly Arg Leu Arg Pro Glu Asp Thr Ala Val Tyr Tyr Cys
            85              90              95 gtg agt gat gct ttt gat gtc tgg ggc cag ggg aca atg gtc acc gtc        336
Val Ser Asp Ala Phe Asp Val Trp Gly Gln Gly Thr Met Val Thr Val
            100             105             110 tct tcg                                                                 342
Ser Ser
```

<210> SEQ ID NO 12
<211> LENGTH: 114
<212> TYPE: PRT
<213> ORGANISM: Homo sapiens

<400> SEQUENCE: 12

```
Glu Val Gln Leu Val Glu Thr Gly Gly Gly Leu Val Pro Pro Gly Gly
1               5                   10                  15

Ser Leu Arg Leu Ser Cys Ala Ala Ser Gly Phe Thr Phe Thr Asn Tyr
            20                  25                  30

Ser Met His Trp Val Arg Leu Ala Pro Gly Lys Arg Leu Glu Tyr Ile
        35                  40                  45

Ser Ala Ile Ser Ser Asp Gly Gly Asp Pro Phe Tyr Ala Ser Ser Val
    50                  55                  60

Lys Gly Arg Val Ala Ile Ser Arg Asp Asn Ser Lys Lys Thr Leu Tyr
65                  70                  75                  80

Leu Gln Met Gly Arg Leu Arg Pro Glu Asp Thr Ala Val Tyr Tyr Cys
            85                  90                  95

Val Ser Asp Ala Phe Asp Val Trp Gly Gln Gly Thr Met Val Thr Val
            100                 105                 110

Ser Ser
```

<210> SEQ ID NO 13
<211> LENGTH: 5
<212> TYPE: PRT
<213> ORGANISM: Homo sapiens

<400> SEQUENCE: 13

```
Asn Tyr Ser Met His
1               5
```

<210> SEQ ID NO 14
<211> LENGTH: 17
<212> TYPE: PRT
<213> ORGANISM: Homo sapiens

<400> SEQUENCE: 14

```
Ala Ile Ser Ser Asp Gly Gly Asp Pro Phe Tyr Ala Ser Ser Val Lys
1               5                   10                  15

Gly
```

<210> SEQ ID NO 15
<211> LENGTH: 5
<212> TYPE: PRT
<213> ORGANISM: Homo sapiens

<400> SEQUENCE: 15

```
Asp Ala Phe Asp Val
1               5
```

<210> SEQ ID NO 16
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: NG034 variable kappa chain (VK) sequence

<400> SEQUENCE: 16

```
gaa att gtg ctg acc cag tct cca ctc tcc ctg tcc gtc acc ctt gga      48
Glu Ile Val Leu Thr Gln Ser Pro Leu Ser Leu Ser Val Thr Leu Gly
1               5                   10                  15 cag ccg gcc tcc atc tcc tgc agg tct agt caa agc ctc cta tac agt      96
Gln Pro Ala Ser Ile Ser Cys Arg Ser Ser Gln Ser Leu Leu Tyr Ser
                20                  25                  30 aat ggc aac acc tac ttg aat tgg ttt cag cag agg cca ggc caa tct     144
Asn Gly Asn Thr Tyr Leu Asn Trp Phe Gln Gln Arg Pro Gly Gln Ser
            35                  40                  45 cca agg cgc cta ctt tat agg gtt tct aac cgg gac tct ggg gtc cca     192
Pro Arg Arg Leu Leu Tyr Arg Val Ser Asn Arg Asp Ser Gly Val Pro
        50                  55                  60 gac aga ttc agc ggc agt ggg tca ggc act cat ttc aca ctg aaa att     240
Asp Arg Phe Ser Gly Ser Gly Ser Gly Thr His Phe Thr Leu Lys Ile
65                  70                  75                  80 agt agg gtg gag gct gag gat gtt gga gtt tat tac tgc atg caa ggt     288
Ser Arg Val Glu Ala Glu Asp Val Gly Val Tyr Tyr Cys Met Gln Gly
                85                  90                  95 aca cac tgg cct cgc acg ttc ggc caa ggg acc aag gtg gag atc aaa     336
Thr His Trp Pro Arg Thr Phe Gly Gln Gly Thr Lys Val Glu Ile Lys
                100                 105                 110
```

<210> SEQ ID NO 17
<211> LENGTH: 112
<212> TYPE: PRT
<213> ORGANISM: Homo sapiens

<400> SEQUENCE: 17

```
Glu Ile Val Leu Thr Gln Ser Pro Leu Ser Leu Ser Val Thr Leu Gly
1               5                   10                  15

Gln Pro Ala Ser Ile Ser Cys Arg Ser Ser Gln Ser Leu Leu Tyr Ser
                20                  25                  30

Asn Gly Asn Thr Tyr Leu Asn Trp Phe Gln Gln Arg Pro Gly Gln Ser
            35                  40                  45

Pro Arg Arg Leu Leu Tyr Arg Val Ser Asn Arg Asp Ser Gly Val Pro
        50                  55                  60

Asp Arg Phe Ser Gly Ser Gly Ser Gly Thr His Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Val Glu Ile Lys
                100                 105                 110
```

<210> SEQ ID NO 18
<211> LENGTH: 16
<212> TYPE: PRT
<213> ORGANISM: Homo sapiens

<400> SEQUENCE: 18

```
Arg Ser Ser Gln Ser Leu Leu Tyr Ser Asn Gly Asn Thr Tyr Leu Asn
1               5                   10                  15
```

```
<210> SEQ ID NO 19
<211> LENGTH: 7
<212> TYPE: PRT
<213> ORGANISM: Homo sapiens

<400> SEQUENCE: 19

Arg Val Ser Asn Arg Asp Ser
1               5

<210> SEQ ID NO 20
<211> LENGTH: 9
<212> TYPE: PRT
<213> ORGANISM: Homo sapiens

<400> SEQUENCE: 20

Met Gln Gly Thr His Trp Pro Arg Thr
1               5

<210> SEQ ID NO 21
<211> LENGTH: 7
<212> TYPE: PRT
<213> ORGANISM: Artificial Sequence
<220> FEATURE:
<223> OTHER INFORMATION: minimal epitope recognized by NG004
<220> FEATURE:
<221> NAME/KEY: PEPTIDE
<222> LOCATION: (1)..(7)
<223> OTHER INFORMATION: minimal epitope recognized by antibody NG004

<400> SEQUENCE: 21

Ile Asn Ala Ala Leu Gln Glu
1               5

<210> SEQ ID NO 22
<211> LENGTH: 15
<212> TYPE: PRT
<213> ORGANISM: Artificial Sequence
<220> FEATURE:
<223> OTHER INFORMATION: Peptide 34
<220> FEATURE:
<221> NAME/KEY: PEPTIDE
<222> LOCATION: (1)..(15)
<223> OTHER INFORMATION: Peptide 34: amino acods 133-147 of the Nogo-A
     d20plus region

<400> SEQUENCE: 22

Glu Glu Ile Lys Glu Pro Glu Asn Ile Asn Ala Ala Leu Gln Glu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Peptide 35
<220> FEATURE:
<221> NAME/KEY: PEPTIDE
<222> LOCATION: (1)..(15)
<223> OTHER INFORMATION: Peptide 35: amino acids 137-151 of the Nogo-A
     d20plus region

<400> SEQUENCE: 23

Glu Pro Glu Asn Ile Asn Ala Ala Leu Gln Glu Thr Glu Ala Pro
1               5                   10                  15

<210> SEQ ID NO 24
<211> LENGTH: 15
<212> TYPE: PRT
```

-continued

```
<213> ORGANISM: Artificial Sequence
<220> FEATURE:
<223> OTHER INFORMATION: Peptide 36
<220> FEATURE:
<221> NAME/KEY: PEPTIDE
<222> LOCATION: (1)..(15)
<223> OTHER INFORMATION: Peptide 36: amino acids 141-155 of the Nogo-A
      d20plus region

<400> SEQUENCE: 24

Ile Asn Ala Ala Leu Gln Glu Thr Glu Ala Pro Tyr Ile Ser Ile
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Peptide 33
<220> FEATURE:
<221> NAME/KEY: PEPTIDE
<222> LOCATION: (1)..(15)
<223> OTHER INFORMATION: Peptide 33: amino acids 129-143 of the Nogo-A
      d20plus region

<400> SEQUENCE: 25

Ser Gly Ile Lys Glu Glu Ile Lys Glu Pro Glu Asn Ile Asn Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Peptide 37
<220> FEATURE:
<221> NAME/KEY: PEPTIDE
<222> LOCATION: (1)..(15)
<223> OTHER INFORMATION: Peptide 37: amino acids 145-159 of the Nogo-A
      d20plus region

<400> SEQUENCE: 26

Leu Gln Glu Thr Glu Ala Pro Tyr Ile Ser Ile Ala Cys Asp Leu
1               5                   10                  15

<210> SEQ ID NO 27
<211> LENGTH: 31
<212> TYPE: PRT
<213> ORGANISM: Artificial Sequence
<220> FEATURE:
<223> OTHER INFORMATION: Consensus sequence of petides 33 to 37
<220> FEATURE:
<221> NAME/KEY: PEPTIDE
<222> LOCATION: (1)..(31)
<223> OTHER INFORMATION: Consensus sequence of petides 33 to 37
<220> FEATURE:
<221> NAME/KEY: PEPTIDE
<222> LOCATION: (13)..(19)
<223> OTHER INFORMATION: minimal epitope recognized by NG004

<400> SEQUENCE: 27

Ser Gly Ile Lys Glu Glu Ile Lys Glu Pro Glu Asn Ile Asn Ala Ala
1               5                   10                  15

Leu Gln Glu Thr Glu Ala Pro Tyr Ile Ser Ile Ala Cys Asp Leu
            20                  25                  30
```

ANTI-Nogo-A ANTIBODIES AND METHODS OF MAKING AND USING THEREOF

CROSS-REFERENCE TO RELATED APPLICATIONS

This application is a U.S. National Stage application of PCT/EP2020/080076, filed 26 Oct. 2020, which claims priority to European Patent Application No. 19205006.0, filed 24 Oct. 2019, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 1 Nov. 2022, is named 0369_0003-PCT-US_Sequence_Listing.txt and is 17 kilobytes in size.

FIELD OF THE INVENTION

The present invention generally relates to novel human-derived antibodies as well as fragments, derivatives and biotechnological variants thereof specifically binding to and neutralizing Nogo-A, which are useful in the treatment of diseases and trauma of the central nervous system, including the retinopathies.

BACKGROUND OF THE INVENTION

The central nervous system tissues (CNS), including the retina, has only a limited capacity to regenerate damaged tissue. CNS regeneration is prevented by various cell-intrinsic suppressors of growth signaling as well as by cell-extrinsic mechanisms. The latter include growth inhibitory factors enriched in the glial scar and in myelin. Nogo-A has been identified as one of the myelin-associated factors limiting the amount of recovery and plasticity in damaged central nervous system of both vasculature and neuronal cells (Wälchli et al., PNAS, 2013). It is a member of the reticulon protein family and has at least two biologically active and pharmacologically distinct domains, Nogo-66 and Nogo-AΔ20 both of which have been shown to possess strong inhibitory activity for neurite growth (GrandPre et al., Nature 417 (2002), 547-51; Oertle et al., J. Neurosci. 23 (2003), 5393-406). Thus, blocking the inhibitory activity of Nogo-A has been uncovered as valuable pharmaceutical target for the treatment of disorders or conditions which are accompanied by injury or degeneration of vascular and neuronal elements of CNS tissue by ameliorating and promoting vascular and neuronal repair and growth (reviewed in Pernet, BBA—Molecular Basis of Disease, 2017).

In this context, it has been reported that a murine monoclonal antibody, IN-1, that was raised against NI-220/250, a rat myelin protein which is a potent inhibitor of neurite growth (and subsequently shown to be encoded by the nogo A gene in rats), promotes axonal regeneration and functional recovery after CNS injuries (Schnell and Schwab, Nature 343 (1990), 269-272; Bregman et al., Nature 378 (1995), 498-501, Thallmair et al., Nature Neuroscience 1 (1998), 124-131, and Chen et al., Nature 403 (2000), 434-439). Further attempts to develop therapeutically effective monoclonal antibodies targeting Nogo-A have been made. For example, WO2004/052932 A2 describes the murine antibody 11C7 which has been shown to efficiently block Nogo-A-induced inhibition in vitro and in vivo (Oertle et al.

(2003), supra; Liebscher et al., Annals of Neurology 58 (2005), 706-719). For instance, in living animals, the administration of 11C7 was able to stimulate axonal outgrowth and locomotion recovery following spinal cord lesion in rats and was shown to promote vascular regeneration after ischemic injury in the CNS (Liebscher et al. (2005), supra; Joly et al., Glia 66 (2018), 2079-2093; Rust et al., PNAS 116 (2019), 14270-14279). In addition, in a study by Lindau et al., Brain (2013), it has been observed that intrathecal application of the antibody 11C7 after corticospinal tract transection, or after unilateral subtotal photothrombotic stroke to the sensorimotor cortex (Wahl et al., Science 344 (2014), 1250-5) resulted in a high degree of functional recovery of the fine forelimb movements in adult rats. A large degree of functional recovery of arm-hand function by intrathecal anti-Nogo-A antibody application was also observed in macaque monkeys with cervical spinal cord or motor cortex injuries (Freund et al., Nat Med. 12 (2006), 790-2; Hamadjida et al., Exp Brain Res. 223 (2012), 321-40). Moreover, it could be shown that Nogo-A inactivation improves visual plasticity and recovery after retinal injury; see, e.g., Mdzomba et al., Cell Death and Disease (2018) 9:727.

Further monoclonal anti-Nogo-A antibodies are disclosed in the international applications WO2005/061544 A2 (the murine antibody 2A10 and the humanized version thereof H1 L11), WO2007/068750 A2 and WO2009/056509 A1 (ATI355, derived from monoclonal antibody 6A3 that was generated in the HuMabmouse™; this genetically reconstituted mouse was produced by Medarex Inc, wherein human immunoglobulin genes replace their murine counterparts). Several of these antibodies are subject of clinical trials for the treatment of spinal cord injury (SCI), amyotrophic lateral sclerosis (ALS) and multiple sclerosis (MS); see Schmandke et al. (2014), supra, and Kucher et al., Neurorehabil. Neural Repair. (2018), 578-589. ATI335 is also designated NG-101 and currently investigated in a multicenter, multinational, placebo controlled phase-II study for the safety and preliminary efficacy in patients with acute cervical Spinal Cord Injury (SCI), in particular if an antibody therapy can improve motor function and quality of life of tetraplegic patients, wherein the antibody is administered by intrathecal bolus injections of 45 mg; see, e.g., ClinicalTrials.gov Identifier: NCT03935321.

In summary, the development of monoclonal anti-Nogo-A antibodies so far holds great promise for the prophylactic or therapeutic treatment of disorders or conditions which are accompanied by injury or disorders or degeneration of the central nervous system (CNS) including the retina, such as spinal cord injury (SCI), stroke or retinopathies incl. retino-vasculopathies.

However, for monoclonal antibodies, product origin is an important factor that can influence immunogenicity. Although mouse antibodies have been shown to robustly elicit immune responses in humans as compared to chimeric, humanized and human monoclonal antibodies, it should be noted that chimeric, humanized and human monoclonal antibodies can also elicit a high rate of immunogenicity depending on the dosing regimen and patient population. In fact, some human antibodies developed using phage display and even fully "human" antibodies derived from transgenic mice may have significant anti-drug antibody (ADA) responses; see, e.g., Harding et al., MAbs. 2010 May-June; 2(3): 256-265 and "Immunogenicity Assessment for Therapeutic Protein Products", U.S. Department of Health and Human Services Food and Drug Administration Center for Drug Evaluation and Research (CDER) Center for Biologics Evaluation and Research (CBER) August 2014 Clinical/

Medical. Accordingly, in several cases persistently positive ADA in a significant number of patients resulted in treatment discontinuation; see, e.g., Kuriakose et al., J. Immunology Research (2016), Article ID 1298473, dx.doi.org and Davda et al. J. ImmunoTherapy of Cancer (2019) 7:105, doi.org.

In this context, immunogenicity of monoclonal antibodies may also be due to impurities and heterogeneity of the antibody preparation, for example because of chemical degradation products of the antibody and thus lack of stability of the antibody molecule; see, e.g., Doevendans and Schellekens, Antibodies 8 (2019), 21; doi.org.

SUMMARY OF THE INVENTION

The present invention relates to the embodiments as characterized in the claims, disclosed in the description and illustrated in the Examples and Figures further below. Thus, the present invention relates to Nogo-A specific human-derived monoclonal antibodies and Nogo-A binding fragments thereof as well as equivalent synthetic variants and biotechnological derivatives of the antibodies exemplified herein, which are particularly useful in the prophylactic or therapeutic treatment of diverse disorders or conditions which are accompanied by injury or disorders or degeneration of the central nervous system (CNS) including the retina and peripheral nervous system (PNS) tissue.

As illustrated in the Examples, within a complex antibody discovery process fortunately a high affinity human mono-clonal anti-Nogo-A antibody could be cloned and identified, which is capable of neutralizing the biological activity of Nogo-A, e.g., by enhancing the growth of neurites in presence of growth inhibitory CNS myelin, by enhancing the functional recovery of the impaired forelimb of adult rats after large, unilateral motor cortex strokes, or by increasing angiogenesis in the penumbra after stroke injury in a mouse model of stroke. This antibody is at least as effective as the previously established mouse anti-Nogo-A antibody "11C7" which is regarded as the "gold standard", for example in stroke studies resulting in functional recovery of skilled forelimb use after stroke. In particular, experiments performed within the scope of the present invention demonstrate that angiogenesis is induced by the anti-Nogo-A antibody of the present invention within the penumbra of adult mice after a permanent stroke of the motor cortex; see, e.g., Example 9. Accordingly, the anti-Nogo-A antibody of the present invention can be generally characterized by a pro-angiogenic effect and by being capable of promoting vascular repair/growth in the ischemic border zone up to three weeks after injury. In addition, or alternatively the anti-Nogo antibody of the present invention may be characterized by being capable of forming and having a pronounced effect on increasing the number of newly formed vascular endothelial cells compared to a control; see, e.g., Example 9.

In summary, the experiments performed in accordance with the present invention were successful in identifying a potent anti-Nogo-A antibody for neurite outgrowth and regeneration, and for functional and vascular repair, e.g., following stroke.

Moreover, as could be shown in further experiments performed in accordance with the present invention, the anti-Nogo-A antibody of the present invention is highly soluble in common buffers such as phosphate buffered saline (PBS) (at least up to 20 mg/ml in PBS) and particularly stable, for example repeated freeze-thaw cycles (PBS solution pH 7.4, 7 mg/ml) did not lead to detectable levels of aggregation and degradation products; see, e.g., Example 10 and FIG. 9.

Surprisingly, though the antibody of the present invention binds the Nogo-AΔ20 (d20) domain (which stretches over >160 amino acids) and is at least as effective as anti-Nogo-A antibody 11C7, it recognizes an epitope which is different from the epitopes of 11C7 and other known anti-Nogo-A antibodies Ozanezumab and ATI355, and does not compete with antibody 11C7 for binding to Nogo-A. In particular, as shown in Example 3, antibody NG004 of the present invention binds the extended d20plus region plus some additional amino acids C- and N-terminal of the inhibitory region (human amino acid position 543-866). Epitope mapping identified a sequence within the human Nogo-A d20plus region including the amino acids 141-INAALQE-147 (SEQ ID NO: 21) which correspond to amino acids 683-689 of the native Nogo-A protein as the minimal epitope recognized by antibody NG004 of the invention; see Example 4 and FIG. 3. Therefore, in one embodiment, the antibody binds a Nogo-A epitope which comprises the amino acid sequence INAALQE (SEQ ID NO: 21); see Example 4 Accordingly, the present invention relates to an antibody or binding fragment thereof having the same binding specificity as antibody NG004, i.e. which has the characteristics to enhance the growth of neurites in presence of growth inhibitory CNS myelin and/or to increase angiogenesis in the penumbra after stroke injury in a mouse model of stroke; and wherein the antibody or binding fragment thereof preferably binds the Nogo-AΔ20 (d20) domain and in particular the amino acid sequence 141-INAALQE-147 (SEQ ID NO: 21). The mentioned features can be easily determined in accordance with the experiments and assays disclosed in the appended Examples, wherein antibody NG004 can be used as reference antibody. Typically, such antibody will compete with the corresponding reference antibody for binding Nogo-A at the same epitope and the peptide, respectively.

Thus, in one embodiment, the antibody of the present invention is derived from antibody NG004 and may be characterized by the complementarity determining regions (CDRs) or hypervariable regions of the variable heavy (VH) and variable light (VL) chain comprising the amino acid sequence of SEQ ID: 2 and SEQ ID NO: 7 or SEQ ID NO: 12 as shown in FIG. 1A and explained in the Figure legend to FIG. 1 below. In another embodiment, the antibody of the present invention is derived from antibody NG034 and may be characterized by the CDRs or hypervariable regions of the VH and VL chain comprising the amino acid sequence of SEQ ID NO: 12 and SEQ ID NO: 17 as shown in FIG. 1B and explained in the Figure legend to FIG. 1 below.

Further experiments performed within the scope of the present invention revealed that the antibody of the present invention is capable of immunostaining cells and tissues expressing Nogo-A. In particular, it has been shown by immunofluorescence staining that the human oligodendro-cyte cell line MO3.13 (expressing Nogo-A intracellularly as well as on the cell surface) and the rat neuronal cell line Neuroscreen-1 (NS-1) as well as oligodendrocytes and motoneurons in rat CNS tissue were positively stained by NG004 to a similar extent as with the positive control antibodies 11C7 and Ozanezumab. Within the course of experiments performed in accordance with the present invention, it has been further shown that the antibody NG004 of the present invention is at least as efficient as antibody 11C7, hitherto used as gold standard, for example having an IC50 for inducing neurite outgrowth in presence of Nogo-A containing growth inhibitory CNS myelin below 15 nM and even below 12 nM; see Example 8.

Therefore, based on the results obtained in the experiments performed within the scope of the invention a novel class of anti-Nogo antibodies is provided which are therapeutically useful in the treatment of disorders associated with undesired Nogo-A activity.

While the invention is illustrated and described by way of reference to the human-derived antibody originally obtained in the experiments performed in accordance with the present invention and described in the Examples it is to be understood that the antibody or antibody fragment of the present invention includes synthetic and biotechnological derivatives of an antibody which means any engineered antibody or antibody-like Nogo-A binding molecule, synthesized by chemical or recombinant techniques, which retains one or more of the functional properties of the subject antibody, in particular its neutralizing activity towards Nogo-A. Thus, while the present invention may be described for the sake of conciseness by way of reference to an antibody, unless stated otherwise synthetic and biotechnological derivatives thereof as well as equivalent Nogo-A binding molecules are meant and included within the meaning of the term "antibody".

Further embodiments of the present invention will be apparent from the description and Examples that follow.

BRIEF DESCRIPTION OF THE DRAWINGS

FIG. 1: Amino acid sequences of the variable regions, i.e. heavy chain and kappa light chain (VH, VL) of anti-Nogo-A specific human antibodies NG004 (A) and NG034 (B) of the present invention. Framework (FR) and complementarity determining regions (CDRs) are indicated with the CDRs being underlined. The Kabat numbering scheme was used (cf. www.bioinf.org.uk; Kabat et al., U.S. Dept. of Health and Human Services, "Sequence of Proteins of Immunological Interest" (1983) referred to in the mentioned web reference and given in Table 1 of WO 2015/092077 A1 at page 28, incorporated herein by reference. Unless otherwise specified, references to the numbering of specific amino acid residue positions in an antibody or Nogo-A-binding fragment, variant, or derivative thereof of the present invention are according to the Kabat numbering system, which however is theoretical and may not equally apply to every antibody of the present invention. For example, depending on the position of the first CDR the following CDRs might be shifted in either direction. Accordingly, in case of any inadvertent errors or inconsistencies regarding indication of CDRs in FIG. 1 and/or the sequence listing the person skilled in the art on the basis of the disclosure content of the present application, i.e. the variable heavy (VH) and variable light (VL) chain amino acid sequences of antibodies NG004 and NG034 is well in the position to determine the correct CDR sequences in accordance with Kabat, which shall be used for defining the claimed antibody and Nogo-A-binding fragment thereof. Depicted are the variable heavy chain VH and light chain VL sequence of antibody NG004 as set forth in SEQ ID NOs: 2 and 7 (A) and of antibody NG034 as set for in SEQ ID NOs: 12 and 17 (B). As further explained in the description, within CDRs and/or framework region conservative amino acid substitutions are preferred which take into account the physicochemical properties of the original amino acid either alone or with an adjacent amino acid as illustrated in Mirsky et al., Mol. Biol. Evol. 32 (2014) 806-819 at page 813, FIG. 6 in particular the AB or LG model, for example such that the position of two amino acids is exchanged.

FIG. 3: Nogo-A binding epitopes of antibody NG004 assessed by pepscan analysis. Pepscan image of NG004. NG004 binding occurred at peptides 34, 35 and 36 (white box) covering amino acids 141-147 of the Nogo-A d20plus region (peptide 34:133-EEIKEPENINAALQE-147 SEQ ID NO: 22, peptide 35: 137-EPENINAALQETEAP-151 SEQ ID NO: 23, peptide 36:141-INAALQETEAPYISI-155 SEQ ID NO: 24, consensus binding sequence: 141-INAALQE-147 SEQ ID NO: 21).

FIG. 6: The effect of NG004 on long-term potentiation (LTP) has been analyzed in an ex vivo assay in mouse hippocampi. (A) Antibody 11C7 used as positive control results in increased LTP by blocking Nogo-A. FG12 is an inactive control antibody. (B) Antibody NG004 demonstrates similar ex vivo activity as 11C7, i.e. increases LTP. (C) Higher dose of NG004 (25 μg/ml) increases the effect size and onset of action.

FIG. 7: In vitro neurite outgrowth assay of NIE mouse neuroblastoma cells in presence or absence of growth inhibitory CNS myelin extract and anti-Nogo-A antibodies. (A, B) NG004 stimulates neurite outgrowth in the presence of rat spinal cord extract (SCE) in a dose dependent manner, very similar to antibody 11C7. (C, D) NG004 and NG034 stimulate neurite outgrowth in the presence of CNS extract of a non-human primate (CNSE), very similar to antibody ATI355. The respective inactive control antibody 3.1 IgG1 has no effect.

FIG. 9: Size exclusion chromatography analyses of NG004 following repeated freeze-thaw cycles and at different pH values shows that the antibody is highly stable.

FIG. 10: Functional recovery after ischemic stroke and 2-week anti-Nogo-A treatment. Rats received a unilateral photothrombotic stroke and were treated continuously (2 ml) intrathecally for two weeks with an osmotic mini pump with either two different anti-Nogo-A antibodies (11C7 [4 mg/ml]; NG004 [4 mg/ml or 8 mg/ml]), or a control antibody (BrdU antibody, 4 mg/ml). Horizontal ladder success score evaluation (impaired forelimb: correct steps/total steps) of the different treatment groups. (A) Timeline of weekly horizontal ladder performance after injury. (B) Performance on day 63 after injury. Animals treated with NG004 8 mg showed a significant improvement compared to anti-BrdU treated animals. NG004 4 mg animals showed a clear trend of improvement.

DETAILED DESCRIPTION OF THE INVENTION

Figure 2:
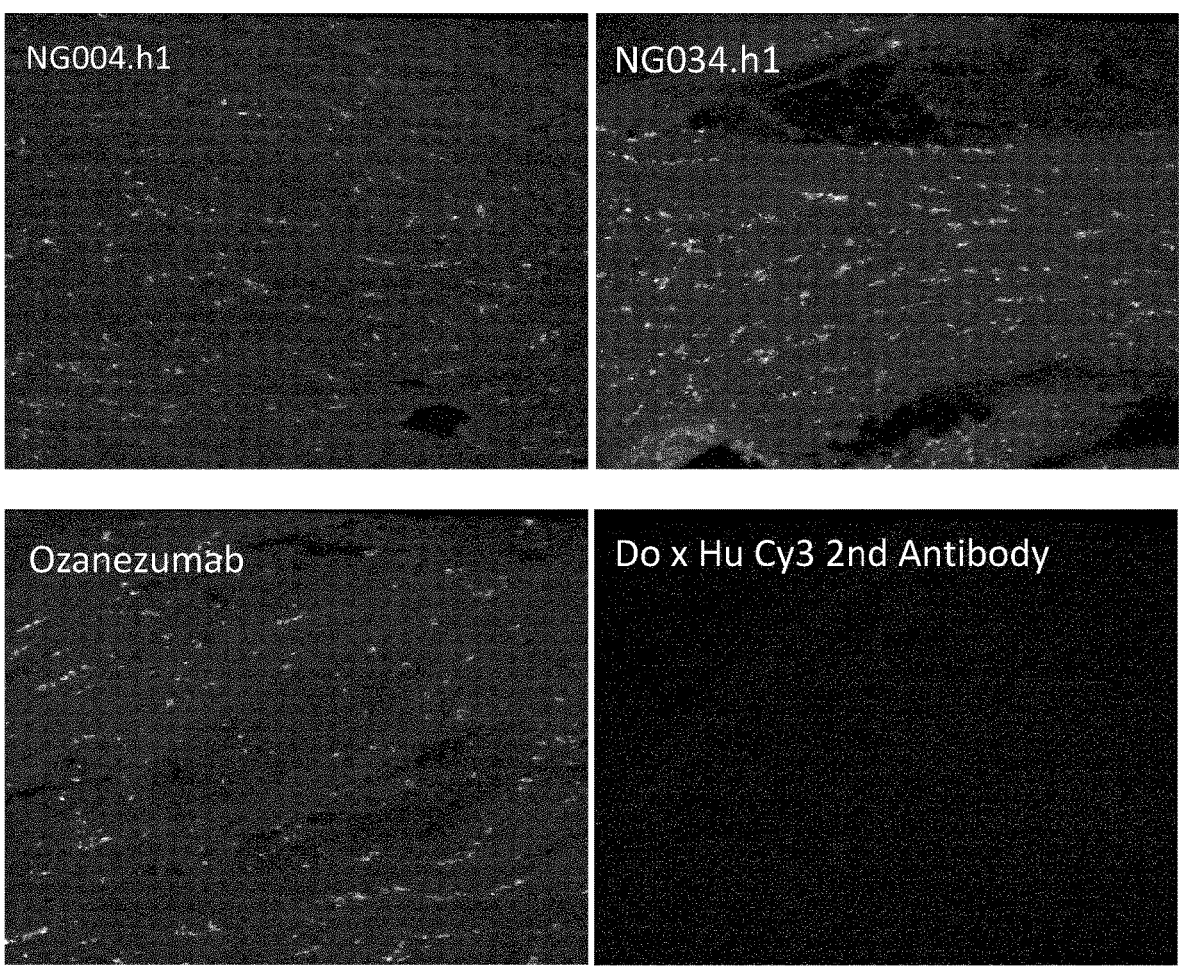
FIG. 2: Binding specificity of antibodies NG004 and NG034 to the d20plus region of recombinantly expressed human and rat Nogo-A. and rat corpus callosum oligodendrocytes. (A) NG004 binds the human Nogo-A d20plus region with high affinity/avidity. The $EC_{50}$ value of NG004 is 0.26 nM. (B) NG004 weakly binds the rat Nogo-A d20plus region. (C) NG034 binds the human Nogo-A d20plus region with high affinity/avidity ($EC_{50}$ value of NG034 is 0.298 nM). (D) NG034 binds the rat Nogo-A d20plus region with high affinity/avidity ($EC_{50}$ value of NG034 is 0.229 nM). (E) NG004 and NG034 positively stain rat corpus callosum oligodendrocytes as shown by immunofluorescence staining on fixed rat brain tissue sections resulting in a staining pattern similar to that of the control antibody Ozanezumab. No staining is observed with the secondary donkey anti-human Cy3-labelled (DoxHu Cy3) antibody alone.

Generally, the present invention relates to human-derived monoclonal antibodies that bind to and are capable of neutralizing Nogo-A as well as fragments, derivatives and variants thereof. More specifically, the present invention relates to the embodiments as characterized in the claims, disclosed in the description and illustrated in the Examples and Figures further below. Due to their human origin, i.e. maturation of the original antibodies in the human body, and their neutralization capacity towards Nogo-A, the antibodies are of high therapeutic value and preferably substantially non-immunogenic in human.

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2; Second edition published 2006, ISBN 0-19-852917-1 978-0-19852917-0.

Furthermore, unless stated otherwise, terms and expressions used herein in order to characterize the present invention are given the definitions as provided in WO 2015/092077 A1, in particular in subsection "I. Definitions" at pages 16 to 42, including Table 1 for the CDR Definitions at page 28, the disclosure content of which is explicitly incorporated herein by reference. The same applies to the general embodiments disclosed in WO 2015/092077 A1 for antibodies, polynucleotides, etc. In addition, without admitting that the scientific publications and patent applications cited in the "Background of the invention" represent prior art as to the present invention as claimed, their disclosure content concerning Nogo-A and anti-Nogo-A antibodies, their recombinant production in a host cell, purification, modification, formulation in a pharmaceutical composition and therapeutic use as well as terms and feature common in the art can be relied upon by the person skilled in art when carrying out the present invention as claimed; see, e.g., Antibodies A Laboratory Manual $2^{nd}$ edition, 2014 by Cold Spring Harbor Laboratory Press, Cold Spring Harbor, New York, USA, wherein also antibody purification and storage; engineering antibodies, including use of degenerate oligonucleotides, 5'-RACE, phage display, and mutagenesis, immunoblotting protocols and the latest screening and labeling techniques are described.

The term "neutralizing" and "neutralizing antibody", respectively, is used as common in the art in that an antibody is meant that reduces or abolishes at least some biological activity of an antigen or of a living microorganism. For example, an anti-Nogo-A antibody of the present invention is a neutralizing antibody, if, in adequate amounts, it abolishes or reduces the activity of Nogo-A for example in an assay as described in the Examples. Neutralization is commonly defined by 50% inhibitory concentrations (IC 50) and can be statistically assessed based on the area under the neutralization titration curves (AUC). IC 50 values of exemplary anti-Nogo-A antibodies of the present invention are described and shown herein, e.g., in FIGS. 5-8. In particular, the neutralization capacity of the antibody of the present invention was and can be analyzed as shown, e.g., in Examples 6-9 in that the antibody downregulates endogenous Nogo-A in vivo in the CNS as determined by immunohistochemistry, increases long-term synaptic plasticity (long-term potentiation, LTP) as determined in an LTP assay in mouse hippocampi, stimulates neurite outgrowth in an in vitro neurite outgrowth assay and induces angiogenesis in the penumbra of an in vivo mouse stroke model.

Accordingly, the present invention generally relates to human-derived recombinant monoclonal anti-Nogo-A antibodies and antigen-binding fragments thereof which neutralize the biological activity of Nogo-A and are capable of inducing dose dependent neurite outgrowth in presence of outgrowth inhibitory CNS extracts for example as demonstrated in Example 8 and/or angiogenesis in stroke penumbra for example as demonstrated in Example 9.

Glia-derived axonal growth inhibitory proteins limit functional repair following damage to the adult CNS. Amongst others, Nogo-A and for example MAG and OMgp are inhibitors which interact with neuronal (co-)receptors, e.g., with NogoA receptors such as Nogo receptor-1 (NgR1), sphingolipid receptor S1PR2 or the Leucine rich repeat and Immunoglobin-like domain-containing protein also known as LINGO-1, leading to inhibition of axonal growth. For example, upon interaction with an inhibitory protein (e.g., Nogo-A), the NgR1 complex transduces signals that lead to growth cone collapse and inhibition of neurite outgrowth. As mentioned above, an in vivo study of intrathecal administration of NG004 in rats demonstrated a significant decrease of Nogo-A in CNS tissue compared to control antibody treatment. Thus, in contrast to the known mechanism to inhibit receptor binding of the ligand Nogo-A, the antibody of the present invention also reduces the ligand from the system, namely by downregulating Nogo-A levels in the CNS, and therefore, demonstrating a potent biological effect.

The in vivo study of intrathecal administration of NG004 in rats further demonstrated that the Nogo-A receptor NgR1 was upregulated (see FIG. 5 C) suggesting that NG004 binds to Nogo-A in vivo and induces a downregulation of the CNS Nogo-A levels and an upregulation of its receptor NgR1 as a compensation mechanism. Thus, a treatment approach using anti-Nogo-A antibodies, preferably antibody NG004 or NG034, might be further improved when combined with a molecule that also inhibits Nogo-A receptor binding to Nogo-A, for example NgR1, S1PR2 or LINGO-1. In particular, the anti-Nogo-A antibody of the present invention, i.e. NG004 and NG034, removes Nogo-A from the system and Nogo-A receptors, like NgR1, S1PR2 or LINGO-1 do not get stimulated. This mechanism is similar to the one of AXER-204, which is a recently developed soluble human fusion protein that acts as a decoy, or trap, for myelin-associated growth inhibitors like MAG, OMgp and Nogo-A, preventing their signaling and promoting neuronal growth; see Bradbury and Oliveira, *Brain* 143 (2020), 1618-1622. Accordingly, it is prudent to expect that the anti-Nogo antibodies of the present invention can be used for the treatment of diseases that can be treated with AXER-204.

Accordingly, in a further aspect the present invention relates to a combination therapy applying an anti-Nogo-A antibody, preferably NG004 or NG034, in combination with a molecule which inhibits binding to Nogo-A to its receptor complexes or blockers of post-receptor signalling pathways for use in the treatment of a disease or trauma of the peripheral (PNS) and/or central (CNS) nervous system as defined herein. Molecules that inhibit Nogo-A receptor binding are known in the art. For example, an isolated polypeptide fragment which inhibits NgR1-mediated neurite outgrowth inhibition is described in WO 2007/089601 A1 or the lateral olfactory tract usher substance (LOTUS) which binds to NgR1 and blocks the binding of Nogo-A to NgR1, resulting in the suppression of axonal growth inhibition induced by Nogo-A is described in Kurihara and Takei, Neural Regen Res. 10 (2015), 46-48. Furthermore, the anti-LINGO-1 antibody Li81 (opicinumab) blocks LINGO-1 function and shows robust remyelinating activity in animal models. This antibody is currently being investigated in a Phase 2 clinical trial as a potential treatment for individuals with relapsing forms of multiple sclerosis; see Hanf et al., mAbs 12(1) (2020), 1713648.

Similar to Nogo-A, the myelin-associated glycoprotein (MAG) and the oligodendrocyte myelin glycoprotein (OMgp) have an axon-inhibitory role and thus, treatment with the anti-Nogo-A antibody of the present invention can be combined with anti-MAG and/or anti-OMgp antibodies; see for example Yu et al., Transl. Stroke Res. 4 (2013), 477-483 and Irving et al., J Cereb Blood Flow Metab. 25 (2005), 98-107.

Furthermore, as demonstrated, e.g., for antibody NG004 in Example 8 the antibody of the present invention has a particularly high neutralizing activity with low inhibitory concentration ($IC_{50}$). In particular, the $IC_{50}$ value of the antibody of the invention for stimulating neurite outgrowth has been shown to be 11.16 nM which is notably lower than the $IC_{50}$ value determined for the reference antibody 11C7 hitherto used as gold standard; see FIG. 7A. Accordingly, in one embodiment, the anti-Nogo-A antibody or antigen-binding fragment thereof shows an $IC_{50}$ value for inducing neurite outgrowth in a neurite outgrowth inhibition assay below 15 nM, preferably 12 nM.

As further illustrated in the Examples and in the Figures, e.g., in FIG. 2, the antibodies of the present invention have been originally isolated from human donors and are shown to bind human Nogo-A. Therefore, in one embodiment the anti-Nogo-A antibody and Nogo-A binding fragment of the present invention is derived from antibody NG004 and recognizes the human Nogo-A d20plus peptide preferentially over the corresponding antigen from other species such as rats or mice. Binding characteristics such as specificity and affinity of the antibodies of the present invention have been tested in several experimental assays as described and shown herein, e.g., in Examples 3 to 5 and in FIGS. 2 to 4. In this context, in order to obtain a measure of the binding affinity, the $EC_{50}$ of the antibodies of the invention in the ELISA performed in Example 3 was determined. As demonstrated, the antibodies of the present invention display a particularly high apparent binding affinity as determined by the $EC_{50}$ value. In particular, the $EC_{50}$ of antibody NG004 for binding human Nogo-A d20plus peptide is 0.26 nM while rat Nogo-A is only weakly bound; see Example 3. In another embodiment, the antibody of the present invention is derived from antibody NG034 recognizes human and rat Nogo-A with high affinity. In particular, the $EC_{50}$ of NG034 is 0.298 nM for binding the human and 0.229 nM for binding the rat d20plus region; see Example 3. Binding of NG004 to human and rat Nogo-A expressed on HEK cells has been further confirmed by immunoprecipitation assays followed by Western blot detection.

Thus, the antibody of the present invention can be preferably characterized by having an $IC_{50}$ value for inducing neurite outgrowth in a neurite outgrowth inhibition assay below 15 nM, preferably below 12 nM, more preferably of about 11 nM and/or an $EC_{50}$ value for binding the human or the rat d20plus region below 0.5 nM, preferably below 0.4 nM, more preferably of about 0.3 nM. However, also depending on the antibody format, for example whether an IgG1, IgG4 or antibody fragments are used, like Fab fragments, the $IC_{50}$ and $EC_{50}$ values may deviate and may be for example higher or lower than the values mentioned above and in the Examples. Accordingly, in this context the term "about" means a value which may differ from the value determined for the reference antibody in the Examples, the difference being preferably less than one order of magnitude and most preferably within the same order of magnitude, for example the $IC_{50}$ may be the reference value±10 nM and the $EC_{50}$ may be the reference value±0.3 nM.

Figure 4:
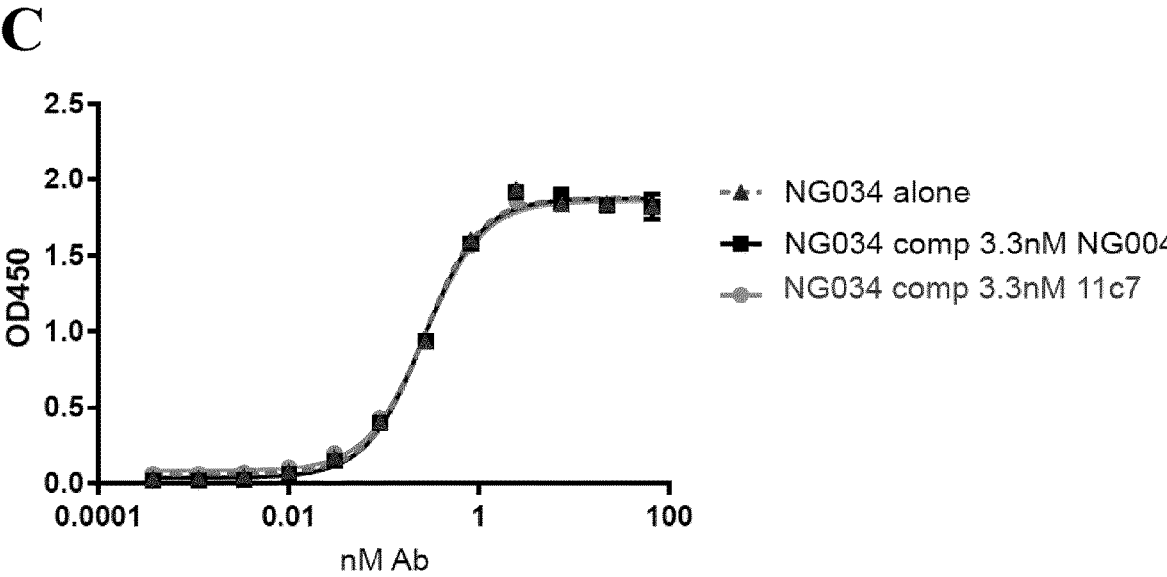
FIG. 4: Cross-competition assay of antibodies NG004 and NG034 for competitive binding to Nogo-A with antibodies Ozanezumab and 11C7. NG004 does not show competitive binding with antibodies Ozanezumab (A) and 11C7 (B). NG034 does not show competitive binding with NG004 and 11C7 in the human d20plus region (C).

As demonstrated in Example 5 and FIG. 4 in a competition assay, the subject antibodies do not show competitive binding to Nogo-A at least with antibody 11C7, and as shown for NG004 preferably also not with Ozanezumab. Accordingly, in one embodiment, the antibody or antigen-binding fragment thereof of the invention, additionally or alternatively does not compete with anti-Nogo-A antibody 11C7 for binding to Nogo-A, and preferably also not with Ozanezumab. Competition between antibodies is determined by an assay in which the immunoglobulin under test is inhibited by specific binding of a reference antibody to a common antigen, such as Nogo-A. Numerous types of competitive binding assays are known; see Harlow and Lane, Antibodies, A Laboratory Manual, Cold Spring Harbor Press (1988), (2014), supra. Preferably, the competitive binding assay is performed under conditions as described in Example 5.

The neurite outgrowth inhibitor Nogo-A contains 3 inhibitory regions. Two are shared with the splice variant Nogo-B (Nogo-66 located between the two transmembrane regions and the NIR domain at the tip of the N-terminus) and one is shared with the splice variant Nogo-C(Nogo-66). The unique, highly inhibitory domain for neurite outgrowth of Nogo-A is located in the exon 3 of Nogo-A and is called delta 20 region (d20; human amino acid position 566-748) (Oertle et al., J. Neurosci. 23 (2003), 5393-5406). As demonstrated in Example 3, the antibodies of the present invention bind to a fragment containing the d20 region (Nogo-A-Δ20 domain) plus some additional amino acids at the C- and N-terminus of the inhibitory region (human amino acid position 543-866), the so-called d20plus region. Accordingly, in one embodiment of the invention, the antibody binds to Nogo-A within the region between amino acid positions 543-866 of human Nogo-A, preferably to an epitope and/or a peptide comprising or consisting of the amino acid sequence 141-INAALQE-147 (SEQ ID NO: 21) corresponding amino acids 683-689 of human Nogo-A; see Example 4.

The present invention is illustrated with anti-Nogo-A antibodies and antigen-binding fragments thereof which are characterized by comprising in their variable region, i.e. binding domain the variable heavy ($V_H$) and variable light ($V_L$) chain having the amino acid sequences depicted in FIGS. 1A and B, respectively. The corresponding nucleotide and amino acid sequences are set forth in Table II below.

As always, the variable domains of each chain contain three hypervariable loops named complementarity determineven more amino acids in case of CDR2 and CDR3. As mentioned in the Figure legend of FIG. 1, the person skilled in the art can easily identify the CDRs according to common principles, for example as summarized in www.bioin-f.org.uk/abs. In this context, while the CDRs of the antibodies depicted in FIG. 1 are indicated according to Kabat et al. the person skilled in the art knows that a number of definitions of the CDRs are commonly in use, i.e. the (i) Kabat definition based on sequence variability, which is the most commonly used;

(ii) Chothia definition based on the location of the structural loop regions;

(iii) AbM definition as a compromise between the two used by Oxford Molecular's AbM antibody modelling software; and (iv) Contact definition that has been recently introduced by and is based on an analysis of the available complex crystal structures. This definition is likely to be the most useful for performing mutagenesis to modify the affinity of an antibody since these are residues which take part in interactions with the antigen. For lists of CDR residues making contact in each antibody with summary data for each CDR see, e.g., www.bioin-f.org.uk/abs which also refers to antibody modelling software such as abYmod available at abymod.aby-sis.org.

Table I below depicts the relation between the CDR positions defined by the different concepts.

TABLE I

| Different concepts of CDR definitons. | | | | |
|---|---|---|---|---|
| Loop | Kabat | AbM | Chothia[1] | Contact[2] | IMGT |
| L1 | L24--L34 | L24--L34 | L24--L34 | L30--L36 | L27--L32 |
| L2 | L50--L56 | L50--L56 | L50--L56 | L46--L55 | L50--L51 |
| L3 | L89--L97 | L89--L97 | L89--L97 | L89--L96 | L89--L97 |
| H1 | H31--H35B (Kabat Numbering)[3] | H26--H35B | H26--H32 . . . 34 | H30--H35B | H26--H35B |
| H1 | H31--H35 (Chothia Numbering) | H26--H35 | H26--H32 | H30--H35 | H26--H33 |
| H2 | H50--H65 | H50--H58 | H52--H56 | H47--H58 | H51--H56 |
| H3 | H95--H102 | H95--H102 | H95--H102 | H93--H101 | H93--H102 |

[1]some of these definitions (particularly for Chothia loops) vary depending on the individual publication examined;
[2]any of the numbering schemes can be used for these CDR defintions, except the contact definition uses the Chothia or Martin (Enhanced Chothia) definition;
[3]the end of the Chothia CDR-H1 loop when numbered using the Kabat numbering convention varies between H32 and H34 depending on the length of the loop. (This is because the Kabat numbering scheme places the insertions at H35A and H35B.)

ing regions (CDRs, CDR-1, -2, and -3). The CDRs are separated by structurally conserved regions called framework regions (FR-1, -2, -3, and -4) that form a "core" ß-sheet structure displaying these loops on the surface of the variable domain. The length and composition of the CDR sequences are highly variable, especially in the CDR3. The CDRs are approximated to the paratope of the antibody that interacts with the antigen and therefore contains the antigen-binding residues. Accordingly, it is common to define an antibody by its six CDRs. Exemplary sets of CDRs in the above amino acid sequences of the $V_H$ and $V_L$ chains are depicted in FIGS. 1A and B. However, as discussed in the following the person skilled in the art is well aware of the fact that in addition or alternatively CDRs may be used, which differ in their amino acid sequence from those set forth in any one of FIGS. 1A and B by one, two, three or For the mentioned definitions see also Kontermann and Dübel (eds.), Antibody Engineering Vol. 2, DOI 10.1007/978-3-642-01147-4_3, #Springer-Verlag Berlin Heidelberg 2010, in particular Chapter 3, Protein Sequence and Structure Analysis of Antibody Variable Domains at pages 33-51 and Dondelinger et al., Front. Immunol. 9 (2018), 2278 specifically dealing with understanding the significance and implications of antibody numbering and antigen-binding surface/residue definition; see, e.g., Dondelinger et al., FIG. 4 and FIG. 6 illustrating the disparity in the classical CDR definitions according to Kabat supra, Chothia (Chothia and Lesk, J. Mol. Biol. 196 (1987), 901-917), Contact (MacCallum et al, J. Mol. Biol. 262 (1996), 732-745) and IMGT (IMGT®, the international ImMunoGeneTics information system®, www.imgt.org). The AbM definition is a compromise between the two used by Oxford Molecular's AbM antibody modelling software.

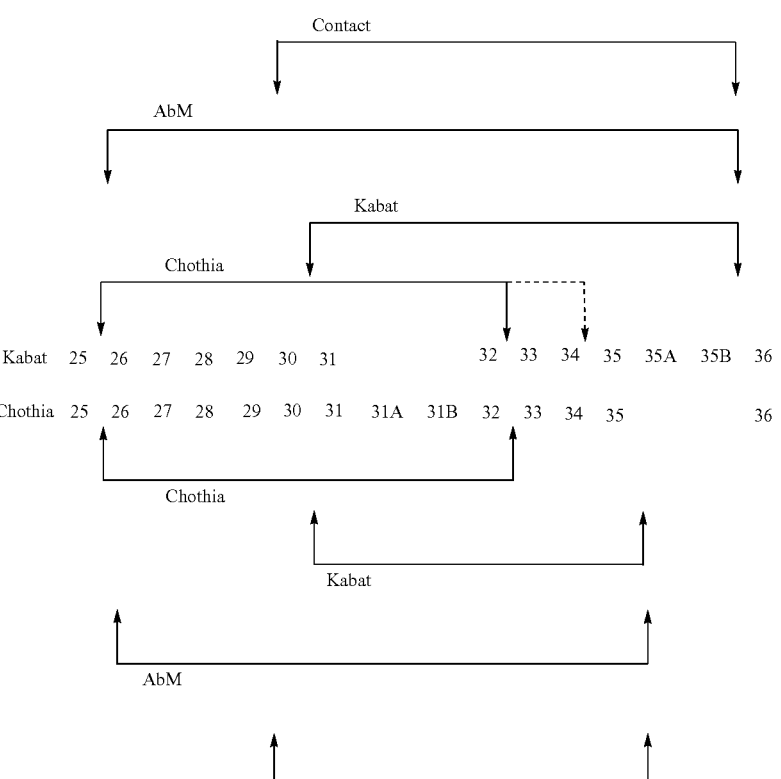

This above diagram illustrates the alternative definitions for CDR-H1 (VH-CDR1). The Kabat and Chothia numbering schemes are shown horizontally and the Kabat, Chothia, AbM and Contact definitions of the CDRs are shown with arrows above and below the two numbering schemes.

In one embodiment, the present invention relates to human-derived monoclonal anti-Nogo-A antibody or Nogo-A binding fragment, synthetic derivative, or biotechnological derivative thereof, wherein the fragment or derivative thereof comprises a variable heavy (VH) chain comprising VH complementary determining regions (CDRs) 1, 2, and 3, and a variable light (VL) chain comprising VL CDRs 1, 2, and 3 as defined by Kabat, wherein (a) VH-CDR1 comprises the amino acid sequence of SEQ ID NO: 3 or a variant thereof, wherein the variant comprises one or two amino acid substitutions, (b) VH-CDR2 comprises the amino acid sequence of SEQ ID NO: 4 or a variant thereof, wherein the variant comprises one or two amino acid substitutions, (c) VH-CDR3 comprises the amino acid sequence of SEQ ID NO: 5 or a variant thereof, wherein the variant comprises one or two amino acid substitutions, (d) VL-CDR1 comprises the amino acid sequence of SEQ ID NO: 8 or a variant thereof, wherein the variant comprises one or two amino acid substitutions, (e) VL-CDR2 comprises the amino acid sequence of SEQ ID NO: 9 or a variant thereof, wherein the variant comprises one or two amino acid substitutions, and (f) VL-CDR3 comprises the amino acid sequence of SEQ ID NO: 10 or a variant thereof, wherein the variant comprises one or two amino acid substitutions; or (g) VH-CDR1 comprises the amino acid sequence of SEQ ID NO: 13 or a variant thereof, wherein the variant comprises one or two amino acid substitutions, (h) VH-CDR2 comprises the amino acid sequence of SEQ ID NO: 14 or a variant thereof, wherein the variant comprises one or two amino acid substitutions, (i) VH-CDR3 comprises the amino acid sequence of SEQ ID NO: 15 or a variant thereof, wherein the variant comprises one or two amino acid substitutions, (j) VL-CDR1 comprises the amino acid sequence of SEQ ID NO: 18 or a variant thereof, wherein the variant comprises one or two amino acid substitutions, (k) VL-CDR2 comprises the amino acid sequence of SEQ ID NO: 19 or a variant thereof, wherein the variant comprises one or two amino acid substitutions, and (l) VL-CDR3 comprises the amino acid sequence of SEQ ID NO: 20 or a variant thereof, wherein the variant comprises one or two amino acid substitutions.

In addition, or alternatively the antibody or antigen-binding fragment thereof of the present can be characterized in that:

(a) the VH chain comprises the amino acid sequence depicted in SEQ ID NO: 2 or a variant thereof, wherein the variant comprises one or more amino acid substitutions; and (b) the VL comprises the amino acid sequence depicted in SEQ ID NO: 7, or a variant thereof, wherein the variant comprises one or more amino acid substitutions; or (c) the VH comprises the amino acid sequence depicted in SEQ ID NO: 12 or a variant thereof, wherein the variant comprises one or more amino acid substitutions; and (d) the VL comprises the amino acid sequence depicted in SEQ ID NO: 17, or a variant thereof, wherein the variant comprises one or more amino acid substitutions;

preferably wherein the VH and VL chain amino acid sequence is at least 90% identical to SEQ ID NO: 2 and 7, respectively. In this embodiment, preferably one or more of the CDRs according to the Kabat definition are maintained substantially unchanged. However, under the simplified assumption that the paratope corresponds to the CDRs, the Chothia definition of the CDRs may be used in addition or alternatively as they correlate very well with the structural loops present in the variable regions. Thus, in order to provide anti-Nogo-A antibodies equivalent to subject antibodies NG004 and NG034, preferably at least one or two of said one or more, preferably not more than two amino acid substitutions if made in the CDRs as defined according to Kabat are made outside the CDRs as defined by Chothia and/or IMGT and most preferably outside the overlap of the CDRs as defined according to Kabat and Chothia.

For example, regarding amino acid substitutions within the CDRs, variable heavy and light chain and framework amino acid sequences, respectively, preferably conservative amino acid substitutions are performed for example in accordance with the most frequently exchanged amino acids as analyzed and described by Mirsky et al., Mol. Biol. Evol. 32 (2014), 806-819; see FIG. 6 at page 813 of Mirsky et al. In particular, within VH-CDR1, S may be substituted with T; within VH-CDR3, V may be substituted with E, T may be substituted with S and/or M may be substituted with V; within VL-CDR1, R may be substituted with K, R may be substituted with E, and/or T may be substituted; within VL-CDR2, S may be substituted with A and/or A may be substituted with G; and in VL-CDR3, P may be substituted with S. As mentioned, preferably amino acid substitutions are selected which belong to the same category in either or preferably both models LG and AB shown in FIG. 6 of Mirsky et al. (2014), supra, with the LG model being preferred for the tendency to keep amino acid properties, and wherein the amino acid substitutions are selected preferably such that the physiochemical properties of the original amino acid is substantially maintained, i.e. hydrophobic, polar or charged property or for example that in case two or more amino acid substitutions are performed, they compensate each other so as to provide the physicochemical property of the surface all together. In a preferred embodiment, the antibody of the invention comprises a variant of the amino acid sequence of the VH and/or VL region which is at least 90%, 95%, 96%, 97%, 98%, 99% or 100% identical to the VH and VL regions depicted in FIGS. 1A and B.

Of course, besides theoretical considerations also experimental approaches exist for identifying CDR variants within a reasonable time and undue burden. For example, Tiller et al., in Front Immunol. 8 (2017), 986 describe facile affinity maturation of antibody variable domains using natural diversity mutagenesis. Indeed, already a few years earlier Rajpal et al., in PNAS 102 (2005), 8466-8471 reported a general method for greatly improving the affinity of antibodies by using combinatorial libraries and illustrated their method with anti-TNF-α antibody D2E7 (HUMIRAC) identifying 38 substitutions in 21 CDR positions that resulted in higher affinity binding to TNF-α. More recently, Cannon et al., in PLOS Computational Biology, doi.org May 1, 2019 described experimentally guided computational antibody affinity maturation with de novo docking, modelling and rational design in silico affinity maturation, together with alanine scanning, that allowed fine-tuning the protein-protein docking model to subsequently enable the identification of two single-point mutations that increase the affinity of a hybridoma-derived antibody, AB1 for its antigen murine CCL20.

Accordingly, though each antibody is unique and may have distinct features, nevertheless once a lead candidate has been provided the person skilled in the art in consideration of the teaching of the present invention as disclosed in the present application, as well as in view of the computational design and experimental approaches developed so far is able to arrive at equivalent anti-Nogo-A antibodies which keep the desired features of the antibody such as those described for the anti-Nogo-A antibodies illustrated in the Examples and specifically defined in the claims. In this context, it is well understood that the variant antibody substantially maintains the binding specificity of the parent antibody, for example competing with the parent antibody for binding Nogo-A while not competing with one or more, preferably all of the mentioned prior art antibodies, i.e. at least not with 11C7, preferably also not with Ozanezumab, which can be assessed in accordance with the competition assay described in Example 5. In particular, an antibody of the invention derived from antibody NG004 does not compete with antibody 11C7 and Ozanezumab. Preferably however, the antibody of the present invention comprises in one or both of its immunoglobulin chains one, two or all three CDRs of the variable regions as set forth in FIG. 1 or one, two or all three CDRs which are 90%, 91%, 92%, 93%, 94%, 95%, 96%, 97%, 98% or 99% identical to the CDRs of the variable regions as set forth in FIG. 1. In addition or alternatively, one or more framework regions (FRs) from the FRs are 80% identical to the corresponding FRs depicted in FIGS. 1A and B, preferably 85%, 90%, 95%, 96, 97%, 98%, 99% or 100% identical to the framework regions depicted in FIGS. 1A and B. In some embodiments, 1, 2, 3, or all 4 FRs (each being at least 90%, 90-95%, and/or 95-99% identical to the FRs shown in FIGS. 1A and B, respectively) are present.

As known in the art, CDR3 of the variable heavy chain (VH-CDR3) seems to mainly determine antigen specificity; see, e.g., Xu and Davis, Immunity 13 (2000), 37-45. In this context, it was noted that it is the diversity of heavy-chain CDR3s that drive specificity, whereas VH-CDR1 and VH-CDR2 residues are broadly cross-reactive and subject to improvement by somatic hypermutation; see Davis, Semin. Immunol. 16 (2004), 239-243. Accordingly, in one embodiment the antibody of the present invention, which has the immunological characteristics of the reference antibody NG004 and being capable of competing with its binding Nogo-A at the respective epitope comprise in their variable region at least VH-CDR3 of the corresponding reference antibody or a VH-CDR3 which amino acid sequence is at least 90% identical to the reference VH-CDR3, preferably 95% identical and, more 96%, 97%, 98%, 99% or 100% identity. For example, a variant antibody of a reference antibody may retain VH-CDR3 of the reference (parent) antibody while VH-CDR1 and/or VH-CDR2 may contain one or more amino acid substitutions; see supra.

In a further additional or alternative embodiment of the present invention the anti-Nogo-A antibody, antigen-binding fragment, synthetic or biotechnological variant thereof can be optimized to have appropriate binding affinity to the target and pharmacokinetic and stability properties. Therefore, at least one amino acid in the CDR or variable region, which is prone to modifications selected from the group consisting of glycosylation, oxidation, deamination, peptide bond cleavage, iso-aspartate formation and/or unpaired cysteine is substituted by a mutated amino acid that lack such alteration or wherein at least one carbohydrate moiety is deleted or added chemically or enzymatically to the antibody, see, e.g. Liu et al., J. Pharm. Sci. 97 (2008), 2426-

2447; Beck et al., Nat. Rev. Immunol. 10 (2010), 345-352; Haberger et al., MAbs. 6 (2014), 327-339.

An immunoglobulin or its encoding cDNA may be further modified. Thus, in a further embodiment, the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988) First edition; Second edition by Edward A. Greenfield, Dana-Farber Cancer Institute @ 2014, ISBN 978-1-936113-81-1. For example, Fab and F(ab')2 fragments may be produced recombinantly or by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes. In one embodiment, the antibody of the present invention may thus be provided in a format selected from the group consisting of a single chain Fv fragment (scFv), an F(ab') fragment, an F(ab) fragment, and an F(ab')2 fragment, an Fd, an Fv, a single-chain antibody, and a disulfide-linked Fv (sdFv) and/or which is a chimeric murine-human or a murinized antibody.

However, as illustrated in the Examples in accordance with the present invention preferably complete IgG antibodies are used, wherein the antibody comprises a constant domain. The constant domain may be native, i.e. originally cloned together with the variable domain or heterologous, for example, a murine constant in case animal studies are envisaged. Preferably, the constant domain is of human origin with a different IgG subtype, e.g. IgG1 versus IgG4 or a different allotype and allele, respectively, compared to the constant domain of the antibody as naturally occurred in human. The definition of "allotypes" requires that antibody reagents are available to determine the allotypes serologically. If the determination is only done at the sequence level, the polymorphisms have to be described as "alleles". This does not hinder to establish a correspondence with allotypes if the correspondence allele-allotype has been experimentally proven, or if the individual sequence is identical to a sequence for which it has been demonstrated.

In a preferred embodiment of the present invention, the constant domain is heterologous to at least one of the CDRs and the VH and VL chains, respectively, e.g. an immunoglobulin heavy chain constant domain and/or immunoglobulin light chain constant domain, preferably of the IgG type. In addition, or alternatively, the heterologous part of the antibody may be a mammalian secretory signal peptide. Put in other words, in one embodiment the anti-Nogo-A antibody and Nogo-A binding fragment, synthetic derivative, and biotechnological derivative thereof of the present invention is a (i) fusion protein comprising a polypeptide sequence which is heterologous to the VH region and/or VL region, or at least one CDR; and/or (ii) a non-natural variant of a polypeptide derived from an immunoglobulin, said non-natural variant comprising a heavy chain constant region that comprises one or more amino acid deletions, substitutions, and/or additions relative to a wild type polypeptide.

As mentioned, five immunoglobulin isotypes exist, of which immunoglobulin G (IgG) is most abundant in human serum. The four subclasses, IgG1, IgG2, IgG3, and IgG4, which are highly conserved, differ in their constant region, particularly in their hinges and upper CH2 domains. These regions are involved in binding to both IgG-Fc receptors (FcgR) and C1q. As a result, the different subclasses have different effector functions, both in terms of triggering FcgR-expressing cells, resulting in phagocytosis or antibody-dependent cell-mediated cytotoxicity, and activating complement. The Fc regions also contain a binding epitope for the neonatal Fc receptor (FcRn), responsible for the extended half-life, placental transport, and bidirectional transport of IgG through mucosal surfaces. However, FcRn is also expressed in myeloid cells, where it participates in both phagocytosis and antigen presentation together with classical FcgR and complement. How these properties, IgG-polymorphisms and post-translational modification of the antibodies in the form of glycosylation, affect IgG-function is described in Vidarsson et al., (2014) IgG subclasses and allotypes: from structure to effector function. Front. Immunol. 5:520. doi:10.3389/fimmu.2014.00520 and de Tacye et al., Antibodies 2019, 8, 30; doi:10.3390/antib8020030. Preferably, the immunoglobulin heavy and/or light chain constant domain present in the antibody of the present invention is of the IgG type, most preferably of the IgG4 class or isotype. Human immunoglobulin G isotype 4 (IgG4) antibodies are potential candidates for antibody therapy when reduced immune effector functions are desirable.

In one embodiment of the antibody of the present invention, the Fc portion may be mutated to decrease immune effector function using techniques known in the art. For example, the deletion or inactivation (through point mutations or other means) of a constant region domain may reduce Fc receptor binding of the modified antibody applied into the cerebrospinal fluid/CNS compartment to the transepithelial transporters of the blood-brain-barrier thereby increasing its Nogo-A protein binding. In other cases, it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced tissue antigen interaction due to increased antigen specificity or antibody flexibility. The resulting physiological profile, bioavailability and other biochemical effects of the modifications, such as Nogo-A protein binding and neutralization, biodistribution and serum half-life, may easily be measured and quantified using well know immunological techniques without undue experimentation. Recombinant human IgG antibodies (hIgGs) completely devoid of binding to Fcγ receptors (FcγRs) and complement protein C1q, and thus with abolished immune effector functions, are of use for various therapeutic applications. It was found that the combination of Leu234Ala and Leu235Ala (commonly called LALA mutations) eliminated FcγRIIa binding and were shown to eliminate detectable binding to FcγRI, IIa, and IIIa for both IgG1 and IgG4 and that the LALA-PG mutation was an improvement over LALA mutations alone in that they nullified Fc function in mouse and human IgG; for corresponding review see, e.g., Saunders (2019) Conceptual Approaches to Modulating Antibody Effector Functions and Circulation Half-Life Front. Immunol. 10:1296.doi: 10.3389/fimmu.2019.01296 and Schlothauer et al., Protein Engineering, Design and Selection 29 (2016), 457-466, IgG4 antibodies are dynamic molecules able to undergo a process known as Fab arm exchange (FAE). This results in functionally monovalent, bispecific antibodies (bsAbs) with unknown specificity and hence, potentially, reduced therapeutic efficacy. As illustrated in the Examples, in a particular preferred embodiment the antibody of the present invention is of the IgG4 class or isotype including the S228P mutation. The S228P mutation prevents in vivo and in vitro IgG4 Fab-arm exchange as demonstrated using a combination of novel quantitative immunoassays and physiological matrix preparation; see Silva et al., J. Biol. Chem. 290 (2015), 5462-5469. As verified in Example 12, NG004 IgG4 S228P indeed shows a reduced reactivity to C1q and behaves similar to other IgG4 antibodies, like Natalizumab.

It is a known problem in the field that repeated freeze-thaw cycles can denature an antibody, causing it to form aggregates that reduce its binding capacity (freeze-thaw damage); see, e.g., the Abcam antibody storage guide. Such antibody deterioration is particularly detrimental for therapeutic antibodies since aggregation or degradation may not only result in reduced antibody activity but also in immunogenic reactions (Ishikawa et al., Biol. Pharm. Bull. 33 (2010), 1413-1417). In contrast, the antibody of the invention is particularly stable. As demonstrated by size exclusion chromatography (SEC), subjecting the antibody to repeated freeze-thaw cycles does not lead to aggregation and degradation after 20× freezing and thawing; see Example 10 and FIG. 9B. In addition, it could be shown that subjecting the antibody of the present invention to different pH values between pH 6 to 8 does not affect the antibody's integrity as determined by SEC; see Example 10 and FIG. 9A. Without being bound by theory, but since previous observations indicated that the constant domain per se is not or not solely responsible for the stability and/or suitability for formulation in a concentration applicable for administration to a human subject, the variable region and in particular the CDRs and VH and VL, respectively, are believed to confer the necessary integrity and stability to the antibody molecule. Therefore, the antibody of the present invention preferably comprises at least the CDRs according to any definition set forth above, preferably according to Kabat and most preferably substantially the entire VH and VL amino acid sequence, respectively, depicted in FIG. 1A or B, which nevertheless may allow for a variation of about 90%, 91%, 92%, 93%, 94%, 95%, 96%, 97%, 99% or 100%, in particular when conservative amino acid substitutions are considered.

The present invention also relates to one or more polynucleotide(s) encoding the antibody or antigen-binding fragment thereof of the present invention or an immunoglobulin VH and VL thereof, preferably wherein the polynucleotide(s) are cDNA.

In a preferred embodiment of the present invention, the polynucleotide comprises, consists essentially of, or consists of a nucleic acid having a polynucleotide sequence encoding the $V_H$ or $V_L$ chain of an anti-Nogo-A antibody as depicted in Table II. In this respect, the person skilled in the art will readily appreciate that the polynucleotides encoding the light and/or heavy chain may be encoded by one or more polynucleotides. In one embodiment therefore, the polynucleotide comprises, consists essentially of, or consists of a nucleic acid having a polynucleotide sequence of the $V_H$ and the $V_L$ chain of an anti-Nogo-A antibody as depicted in Table II.

TABLE II

Nucleotide and amino acid sequences of the variable regions (VH, VL) of the antibodies NG004 and NG034 of the present invention. Underlined, bold nucleotides or amino acids indicate the CDR coding regions in the variable chain sequence.

| Antibody | Nucleotide and amino acid sequence of the variable heavy (VH) and variable light (VL) chains. |
|---|---|
| NG004-VH | gaggtgcagctggtggagtctgggggaggcgtggtccagcct gggaggtccctgagactctcctgtgcagcctctggattcacc ttcaggagccatgctatgcactgggtccgccaggctccaggc aaggggctggagtgggtggcagttacatcatatgatggaacc aataaatactacgcagactccgtgaaggggccgattcaccatc tccaaagacaattccaagaacacgctgtatctgcaaatggac agcctcagagttgaggacacggctgtgtattactgtgcgaga ggccgagcagtggctggtacgagggaagattattggggccag ggaaccctggtcaccgtctcctcg SEQ ID NO: 1 |
| NG004-VH | EVQLVESGGGVVQPGRSLRLSCAASGFTFR SHAMHWVRQAPGKGLEWVA VTSYDGTNKYYADSVKG RFTISKDNSKNTLYLQMDSLRVEDTAVYYCAR GRAVAGTREDYWGQGTLVTVSS SEQ ID NO: 2 |
| NG004-VL | gacatccagatgacccagtctccagactccctggctgtgtct ctgggcgagagggccaccatcaactgcaagtccagccagagt gtttttattcagctccaacagtaagaactacttagcttggtac cagcagaaaccaggacagcctcctaaggtgctcatttactgg gcatctacccgggaatccgggtccctgaccgattcagtggc agcgggtctgggacagatttcactctcaccatcagcagcctg caggctgaagatgtggcagtttattactgtcagcaatattat actactcgccctacgttcggcctagggaccaaagtggatatc aaa SEQ ID NO: 6 |
| NG004-VL | DIQMTQSPDSLAVSLGERATINC KSSQSVLFSSNSKNYLA WYQQKPGQPPKVLIYWASTRES GVPDRFSGSGSGTDFTLTISSLQAEDVAVYYC QQYYTTRPT**FGLGTKVDIK SEQ ID NO: 7 |
| NG034-VH | gaggtgcagctggtggagactggggggaggcttggtcccaccg gggggggtccctgagactctcctgtgcagcctctggattcacc ttcaccaactattctatgcactgggtccgccctggctccaggg aagagactggaatatatttcagctattagtagtgatggcggt gacccattttatgcaagctctgtgaagggcagagtcgccatc tccagagacaattccaagaagacgttgtatcttcaaatgggc agactgagacctgaggacacggctgtatattattgtgtgagt gatgcttttgatgtctggggccagggggacaatggtcaccgtc tcttcg SEQ ID NO: 11 |
| NG034-VH | EVQLVETGGGLVPPGGSLRLSCAASGFTFT NYSMHWVRLAPGKRLEYIS AISSDGGDPFYASSVKG RVAISRDNSKKTLYLQMGRLRPEDTAVYYCVS DAFDVWGQGTMVTVSS SEQ ID NO: 12 |
| NG034-VL | gaaattgtgctgacccagtctccactctccctgtccgtcacc cttggacagcccggcctccatctcctgcaggtctagtcaaagc ctcctatacagtaatggcaacacctacttgaattggtttcag cagaggccaggccaatctccaaggcgcctactttatagggtt tctaaccgggactctggggtcccagacagattcagcggcagt gggtcaggcactcatttcacactgaaaattagtagggtggag gctgaggatgttggagtttattactgcatgcaaggtacacac tggcctcgcacgttcggccaagggaccaaggtggagatcaaa SEQ ID NO: 16 |

TABLE II-continued

Nucleotide and amino acid sequences of the
variable regions (VH, VL) of the antibodies
NG004 and NG034 of the present invention.
Underlined, bold nucleotides or amino acids
indicate the CDR coding regions in the
variable chain sequence.

| Anti-<br>body | Nucleotide and amino acid sequence of<br>the variable heavy (VH) and variable<br>light (VL) chains. |
|---|---|
| NG034-<br>VL | EIVLTQSPLSLSVTLGQPASISC<br>RSSQSLLYSNGNTYLN<br>WFQQRPGQSPRRLLY<br>RVSNRDSGVPDRFSGSGSGTHFTLKISRVEAEDVGVYYC<br>MQGTHWPRTFGQGTKVEIK<br>SEQ ID NO: 17 |

In one embodiment of the present invention, the polynucleotide(s) are linked to a heterologous nucleic acid, for example expression control sequences such as a promoter, transcription and/or translation enhancer sequences, internal ribosome binding sites, nucleic acids encoding a peptide leader sequence for recombinant expression in a host and the like. Accordingly, the present invention relates to a polynucleotide encoding a human-derived recombinant anti-Nogo-A antibody or Nogo-A binding fragment, synthetic derivative, or biotechnological derivative thereof, wherein the polynucleotide encodes (i) a VH chain comprising CDRs 1, 2, and 3, and/or a VL chain comprising VL CDRs 1, 2, and 3 as defined by Kabat, wherein (a) VH-CDR1 comprises the amino acid sequence of SEQ ID NO: 3 or a variant thereof, wherein the variant comprises one or two amino acid substitutions, (b) VH-CDR2 comprises the amino acid sequence of SEQ ID NO: 4 or a variant thereof, wherein the variant comprises one or two amino acid substitutions, (c) VH-CDR3 comprises the amino acid sequence of SEQ ID NO: 5 or a variant thereof, wherein the variant comprises one or two amino acid substitutions, (d) VL-CDR1 comprises the amino acid sequence of SEQ ID NO: 8 or a variant thereof, wherein the variant comprises one or two amino acid substitutions, (e) VL-CDR2 comprises the amino acid sequence of SEQ ID NO: 9 or a variant thereof, wherein the variant comprises one or two amino acid substitutions, and (f) VL-CDR3 comprises the amino acid sequence of SEQ ID NO: 10 or a variant thereof, wherein the variant comprises one or two amino acid substitutions; and/or (ii) a VH chain and/or a VL chain, wherein (a) the VH chain comprises the amino acid sequence depicted in SEQ ID NO: 2 or a variant thereof, wherein the variant comprises one or more amino acid substitutions; and (b) the VL comprises the amino acid sequence depicted in SEQ ID NO: 7, or a variant thereof, wherein the variant comprises one or more amino acid substitutions;

preferably wherein the VH and VL chain amino acid sequence is at least 90% identical to SEQ ID NO: 2 and 7, respectively; or (iii) a VH chain comprising CDRs 1, 2, and 3, and/or a VL chain comprising VL CDRs 1, 2, and 3 as defined by Kabat, wherein (a) VH-CDR1 comprises the amino acid sequence of SEQ ID NO: 13 or a variant thereof, wherein the variant comprises one or two amino acid substitutions, (b) VH-CDR2 comprises the amino acid sequence of SEQ ID NO: 14 or a variant thereof, wherein the variant comprises one or two amino acid substitutions, (c) VH-CDR3 comprises the amino acid sequence of SEQ ID NO: 15 or a variant thereof, wherein the variant comprises one or two amino acid substitutions, (d) VL-CDR1 comprises the amino acid sequence of SEQ ID NO: 18 or a variant thereof, wherein the variant comprises one or two amino acid substitutions, (e) VL-CDR2 comprises the amino acid sequence of SEQ ID NO: 19 or a variant thereof, wherein the variant comprises one or two amino acid substitutions, and (f) VL-CDR3 comprises the amino acid sequence of SEQ ID NO: 20 or a variant thereof, wherein the variant comprises one or two amino acid substitutions; and/or (iv) a VH chain and/or a VL chain, wherein (a) the VH chain comprises the amino acid sequence depicted in SEQ ID NO: 12 or a variant thereof, wherein the variant comprises one or more amino acid substitutions; and (b) the VL comprises the amino acid sequence depicted in SEQ ID NO: 17, or a variant thereof, wherein the variant comprises one or more amino acid substitutions;

preferably wherein the VH and VL chain amino acid sequence is at least 90% identical to SEQ ID NO: 12 and 17, respectively.

In addition, the present invention relates to a polynucleotide linked to a heterologous nucleic acid, wherein the polynucleotide is selected from the group consisting of:

(a) a polynucleotide encoding an immunoglobulin heavy chain or a fragment thereof comprising a heavy chain variable region (VH) comprising CDRs 1, 2, and 3 with the amino acid sequences set forth in SEQ ID NOs: 3, 4, and 5, respectively, and wherein the VH when paired with a light chain variable region (VL) comprising the amino acid sequence set forth in SEQ ID NO: 7 binds to Nogo-A;

(b) a polynucleotide encoding an immunoglobulin light chain or a fragment thereof comprising a VL comprising CDRs 1, 2, and 3 with the amino acid sequences set forth in SEQ ID NOs: 8, 9, and 10, respectively, and wherein the VL when paired with a VH comprising the amino acid sequence set forth in SEQ ID NO: 2 binds to Nogo-A;

(c) a polynucleotide encoding (i) an immunoglobulin heavy chain or a fragment thereof comprising a VH comprising CDRs 1, 2, and 3 with the amino acid sequences set forth in SEQ ID NOs: 3, 4, and 5, respectively; and (ii) an immunoglobulin light chain or a fragment thereof comprising a VL comprising CDRs 1, 2, and 3 with the amino acid sequences set forth in SEQ ID NOs: 8, 9, and 10, respectively;

(d) a polynucleotide encoding an immunoglobulin heavy chain or a fragment thereof comprising a VH comprising the amino acid sequence set forth in SEQ ID NO: 2, wherein the VH when paired with a VL comprising the amino acid sequence set forth in SEQ ID NO: 7 binds to Nogo-A;

(e) a polynucleotide encoding an immunoglobulin light chain or a fragment thereof comprising a VL comprising the amino acid sequence set forth in SEQ ID NO: 7, wherein the VL when paired with a VH comprising the amino acid sequence set forth in SEQ ID NO: 2 binds to Nogo-A;

(f) a polynucleotide encoding an immunoglobulin heavy chain or a fragment thereof comprising a VH comprising the amino acid sequence set forth in SEQ ID NO: 2 and an immunoglobulin light chain or a fragment thereof comprising a VL comprising the amino acid sequence set forth in SEQ ID NO: 7;

(g) a polynucleotide as in any one of (a)-(f), wherein a CDR comprises one or more, preferably no more than two amino acid substitution and/or the variable region sequence is at least 90% identical to SEQ ID NO: 2 or SEQ ID NO: 7.

Alternatively, the present invention relates to a polynucleotide linked to a heterologous nucleic acid, wherein the polynucleotide is selected from the group consisting of:

(a) a polynucleotide encoding an immunoglobulin heavy chain or a fragment thereof comprising a heavy chain variable region (VH) comprising CDRs 1, 2, and 3 with the amino acid sequences set forth in SEQ ID NOs: 13, 14, and 15, respectively, and wherein the VH when paired with a light chain variable region (VL) comprising the amino acid sequence set forth in SEQ ID NO: 17 binds to Nogo-A;

(b) a polynucleotide encoding an immunoglobulin light chain or a fragment thereof comprising a VL comprising CDRs 1, 2, and 3 with the amino acid sequences set forth in SEQ ID NOs: 18, 19, and 20, respectively, and wherein the VL when paired with a VH comprising the amino acid sequence set forth in SEQ ID NO: 12 binds to Nogo-A;

(c) a polynucleotide encoding (i) an immunoglobulin heavy chain or a fragment thereof comprising a VH comprising CDRs 1, 2, and 3 with the amino acid sequences set forth in SEQ ID NOs: 13, 14, and 15, respectively; and (ii) an immunoglobulin light chain or a fragment thereof comprising a VL comprising CDRs 1, 2, and 3 with the amino acid sequences set forth in SEQ ID NOs: 18, 19, and 20, respectively;

(d) a polynucleotide encoding an immunoglobulin heavy chain or a fragment thereof comprising a VH comprising the amino acid sequence set forth in SEQ ID NO: 12, wherein the VH when paired with a VL comprising the amino acid sequence set forth in SEQ ID NO: 17 binds to Nogo-A;

(e) a polynucleotide encoding an immunoglobulin light chain or a fragment thereof comprising a VL comprising the amino acid sequence set forth in SEQ ID NO: 17, wherein the VL when paired with a VH comprising the amino acid sequence set forth in SEQ ID NO: 12 binds to Nogo-A;

(f) a polynucleotide encoding an immunoglobulin heavy chain or a fragment thereof comprising a VH comprising the amino acid sequence set forth in SEQ ID NO: 12 and an immunoglobulin light chain or a fragment thereof comprising a VL comprising the amino acid sequence set forth in SEQ ID NO: 17;

(g) a polynucleotide as in any one of (a)-(f), wherein a CDR comprises one or more, preferably no more than two amino acid substitution and/or the variable region sequence is at least 90% identical to SEQ ID NO: 12 or SEQ ID NO: 17.

Furthermore, the present invention relates to a vector and vectors comprising one or more of those polynucleotides, preferably wherein the vector is an expression vector and the one or more polynucleotides are operably linked to expression control sequences.

The polynucleotides may be produced and, if desired manipulated using methods well known in the art for the manipulation of nucleotide sequences, e.g., recombinant DNA techniques, site directed mutagenesis, PCR, etc. (see, for example, the techniques described in Molecular Cloning: A Laboratory Manual (Fourth Edition): Three-volume set; Green and Sambrook (2012) ISBN 10:1936113422/ISBN 13:9781936113422 Cold Spring Harbor Laboratory Press; update (2014) ISBN 978-1-936113-42-2 and Ausubel et al., eds., Current Protocols in Molecular Biology, John Wiley & Sons, NY (1998) and updates, which are both incorporated by reference herein in their entireties), to generate antibodies having a different amino acid sequence, for example to create amino acid substitutions, deletions, and/or insertions.

Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses, and retroviruses. In general, vectors compatible with the instant invention will comprise a selection marker, appropriate restriction sites to facilitate cloning of the desired gene and the ability to enter and/or replicate in eukaryotic or prokaryotic cells. The marker may provide for prototrophy to an auxotrophic host, biocide resistance (e.g., antibiotics), or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. For the expression of double-chained antibodies, a single vector or vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad Sci. USA 77 (1980), 2197 The coding sequences for the heavy and light chains may comprise cDNA or genomic DNA. The expression vector(s) is (are) transferred to a host cell by conventional techniques and the transfected cells are then cultured by conventional techniques to produce an antibody for use in the methods described herein. Accordingly, the present invention also relates to host cells comprising one or more polynucleotides or a vector or vectors of the present invention.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

Currently, almost all therapeutic antibodies are still produced in mammalian cell lines in order to reduce the risk of immunogenicity due to altered, non-human glycosylation patterns. However, recent developments of glycosylation-engineered yeast, insect cell lines, and transgenic plants are promising to obtain antibodies with "human-like" post-translational modifications. Furthermore, smaller antibody fragments including bispecific antibodies without any glycosylation are successfully produced in bacteria and have advanced to clinical testing. The first therapeutic antibody products from a non-mammalian source can be expected in coming next years. A review on current antibody production systems that can be applied for preparing the human-derived recombinant anti-Nogo-A antibody or Nogo-A binding fragment, synthetic derivative, or biotechnological derivative thereof of the present invention including their usability for different applications is given in Frenzel et al., Front Immunol. 2013; 4:217, published online on Jul. 29, 2013doi: 10.3389/fimmu.2013.00217 and transient expression of human antibodies in mammalian cells is described by Vazquez-Lombardi et al., Nature protocols 13 (2018), 99-117; and Hunter et al., Optimization of protein expression in mammalian cells. Current Protocols in Protein Science 95 (2019), e77. doi: 10.1002/cpps.77.

Once an antibody molecule of the invention has been recombinantly expressed, the whole antibodies, their dimers, individual light and heavy chains, or other immunoglobulin forms of the present invention can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N. Y. (1982) and Antibodies A Laboratory Manual 2nd edition, 2014 by Cold Spring Harbor Laboratory Press, Cold Spring Harbor, New York. USA. Thus, the present invention also relates to a method for preparing an anti-Nogo-A antibody and/or fragments thereof or immunoglobulin chain(s) thereof, said method comprising:

(a) culturing the host cell as defined hereinabove, which cell comprised the polynucleotide(s) or vector(s) as defined hereinbefore under conditions allowing for expression of the anti-Nogo-A antibody, Nogo-A-binding fragment or immunoglobulin chain(s) thereof, and (b) isolating the anti-Nogo-A antibody, Nogo-A-binding fragment or immunoglobulin chain(s) thereof from the culture.

Furthermore, the present invention also relates to the anti-Nogo-A antibody, Nogo-A-binding fragment and immunoglobulin chain(s) thereof encoded by a polynucleotide as defined hereinabove and/or obtainable by the method for their recombinant production mentioned above.

In certain embodiments, the antibody polypeptide comprises an amino acid sequence or one or more moieties not normally associated with an antibody. Exemplary modifications are described in more detail below. For example, the antibody or Nogo-A binding fragment thereof such a single-chain Fv antibody fragment of the invention may comprise a flexible linker sequence, or may be modified to add a functional moiety or detectable label (e.g., PEG, a drug, a toxin, or a label such as a fluorescent, chemiluminescent, radioactive, enzyme, nuclear magnetic, heavy metal, a tag, a flag and the like); see, e.g., Antibodies A Laboratory Manual 2nd edition, 2014 by Cold Spring Harbor Laboratory Press, Cold Spring Harbor, New York, USA for general techniques; Dean and Palmer, Nat Chem Biol. 10 (2014), 512-523, for advances in fluorescence labeling strategies for dynamic cellular imaging; and Falck and Müller, Antibodies 7 (2018), 4; doi: 10.3390/antib7010004 for enzyme-based labeling strategies for antibody-drug conjugates and antibody mimetics.

An antibody polypeptide of the invention may comprise, consist essentially of, or consist of a fusion protein. Fusion proteins are chimeric molecules which comprise, for example, an immunoglobulin Nogo-A-binding domain with at least one target binding site, and at least one heterologous portion, i.e. a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

The human-derived recombinant anti-Nogo-A antibody or Nogo-A binding fragment, synthetic derivative, or biotechnological derivative thereof, optionally as fusion protein and/or labeled as described hereinbefore is then provided for various applications in accordance with standard techniques known in the art; see, e.g., Antibodies A Laboratory Manual 2nd edition, 2014 by Cold Spring Harbor Laboratory Press, Cold Spring Harbor, New York, USA. Current advancements in therapeutic antibody design, manufacture, and formulation are described in Sifniotis et al., Antibodies 2019, 8(2), 36; doi.org, wherein also developments in computational approaches for the strategic design of antibodies with modulated functions are discussed.

The present invention relates to compositions comprising the aforementioned Nogo-A-binding molecule of the present invention, e.g., antibody or Nogo-A-binding fragment, variant or biotechnological derivative thereof, or the polynucleotide(s), vector(s) or cell of the invention as defined hereinbefore. In one embodiment, the composition of the present invention is a pharmaceutical composition and further comprises a pharmaceutically acceptable carrier.

The polynucleotide(s) and the composition of the present invention comprising said polynucleotide(s) can be used for therapeutic approaches. For example, the use of antibody encoding nucleotide sequences in DNA or mRNA form for therapeutics is summarized in Hoecke and Roose, J. Transl. Med. 17 (2019), 54. Those nucleotide sequences can be directly administered to the subject to be treated which allows the in situ production of the respective antibodies. Furthermore, Schlake et al., Cellular and Molecular Life Sciences 76 (2019), 301-328 describe DNA-based antibody expression in vivo as well as corresponding plasmids and viral vectors, for example adeno-associated viruses (AAVs) and mRNA constructs prepared by in vitro transcription (IVT) for use in therapeutic approaches and passive immunotherapy. In general, RNA vaccination is an expanding field with applications from cancer immunotherapy, neurodegenerative diseases, infectious diseases, tissue regeneration and protein replacement therapy.

Accordingly, the polynucleotide(s) of the present invention include RNA and may be used for translation in cells for therapeutics. Thus, the polynucleotide(s), in particular RNA (s) of the present invention can be used for generating the antibodies of the present invention in target cells. Various approaches for the production of suitable RNA are known to the person skilled in the art and are commercially available, e.g., kits for in vitro transcription, capping of RNA and for making poly(A)-tailed mRNA for translation in cells. In WO 2008/083949 A2 antibody-coding non-modified and modified RNA for expression of the corresponding antibody are described as well as transcription methods and methods for expressing the antibody. In WO 2009/127230 A1 modified (m)RNA suitable for suppressing and/or avoiding an innate immunostimulatory response is described. Furthermore, a technology used by CELLSCRIPT™ has been developed, wherein the RNA contains pseudouridine (Ψ) and/or 5-methylcytidine (m5C) in place of the corresponding U or C canonical nucleosides. Such RNA has been shown to be less immunogenic and is translated into protein at much higher levels than the corresponding mRNA that does not contain modified nucleosides. The corresponding technology is described e.g. in Kariko et al., Immunity 23 (2005), 165-175, Karikó et al., Molecular Therapy 16 (2008), 1833-1840 and Anderson et al., Nucleic Acids Res 38 (2010), 5884-5892. Furthermore, EP 1 604 688 A1 describes stabilized and translation optimized mRNA having an enhanced G/C-content and optimized codon usage. Further approaches for the modification of RNA are described for example in Kormann et al., Nature Biotechnology 29 (2011), 154-157 and WO 2007/024708 A2.

Thus, in one embodiment the polynucleotide(s) of the present invention is/are RNA which can be mRNA or derived thereof either unmodified or modified as described above and suitable for translation into the corresponding antibody.

As mentioned above, the present invention relates to a vector comprising the polynucleotide of the present invention. In one embodiment, the vector is a gene transfer vector, for example an adeno-associated virus (AAV) vector. Therapeutic approaches for the treatment of neurodegenerative diseases using AAV vectors are for example described in WO 2015/035190 A1 and Lui et al., The Journal of Neuroscience 36 (2016), 12425-12435 both which relate to AAV-vectored anti-tau antibodies. Such constructs can be used for delivery of genes encoding the antibodies directly to the brain, thus bypassing the blood: brain barrier. Furthermore, WO 2017/189963 A1 describes in general novel AAV particles having viral genomes engineered to encode antibodies and antibody-based compositions and methods of using these constructs (e.g., VAD) for the treatment, prevention, diagnosis and research of diseases, disorders and/or conditions. The progress and clinical applications of AAV in neurodegenerative disease in central nervous system is reviewed in Qu et al., Neural Regen Res 14 (2019), 931-938.

AAV vectors are widely used in gene therapy approaches due to a number of advantageous features. AAVs are non-replicating in infected cells and therefore not associated with any known disease. Furthermore, AAVs may be introduced to a wide variety of host cells, do not integrate into the genome of the host cell, and are capable of infecting both quiescent and dividing cells AAVs transduce non-replicating and long-lived cells in vivo, resulting in long term expression of the protein of interest. Further, AAVs can be manipulated with cellular and molecular biology techniques to produce non-toxic particles carrying a payload encoded in the AAV viral genome that can be delivered to a target tissue or set of cells with limited or no side-effects. Given the foregoing, the use of AAVs for vectored antibody delivery would allow for longer lasting efficacy, fewer dose treatments, and more consistent levels of the antibody throughout the treatment period.

AAV is a member of the Parvoviridae family and comprises a linear, single-stranded DNA genome of less than about 5,000 nucleotides AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368). The AAV vector may be generated using any AAV serotype known in the art. Several AAV serotypes and over 100 AAV variants have been isolated from adenovirus stocks or from human or nonhuman primate tissues (reviewed in, e.g., Wu et al., Molecular Therapy 14(3), (2006), 316).

In addition to the nucleic acid sequence encoding the antibody of the present invention, or an antigen-binding fragment thereof, the AAV vector may comprise expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, Gene Expression Technology: Methods in Enzymology, Vol. 185, Academic Press, San Diego, CA. (1990).

Thus, the invention relates to a gene transfer vector comprising the isolated nucleic acid sequence which encodes the antibody of the present invention. The gene transfer vector may be an adeno-associated virus (AAV) vector as described above.

The present invention also provides the pharmaceutical and diagnostic composition, respectively, in form of a pack or kit comprising one or more containers filled with one or more of the above described ingredients, e.g., anti-Nogo-A antibody, Nogo-A-binding fragment, biotechnological derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate immuno-based diagnostic assays. The composition, e.g. kit of the present invention is of course particularly suitable for the risk assessment, diagnosis, prevention and treatment of a disease or disorder which is accompanied with the presence of Nogo-A, and in particular applicable for the treatment of disorders generally associated with Nogo-A as discussed herein above.

The pharmaceutical compositions of the present invention can be formulated according to methods well known in the art; see for example, Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. As regards RNA-based compositions, in international applications WO 2020/089342 A1, WO 2019/207060 A1 and WO 2018/232355 A1 lipid-based formulations and polymer-based formulations, respectively for efficient administration of RNA to a subject are described. Furthermore, encapsulation of RNA into neutral lipopolyplexes (LPPs) is described in Perche et al., Molecular Therapy: Nucleic Acids 17 (2019). Romani et al., Scientific Reports 7 (2017), 10863 also describe approaches for intravenous administration of RNA-lipoplexes. These pharmaceutical compositions can be administered to the subject at a suitable dose. Administration of the suitable compositions may be effected by different ways, e.g., by intravenous, intraperitoneal, subcutaneous, intramuscular, intranasal, intravitreal, topical or intradermal administration or spinal or brain delivery. Aerosol formulations such as nasal spray formulations include purified aqueous or other solutions of the active agent with preservative agents and isotonic agents. Such formulations are preferably adjusted to a pH and isotonic state compatible with the nasal mucous membranes.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

Due to its growth restricting properties Nogo-A can have negative effects on nervous system injury and disease. Hence, correlating with its various neurobiological roles, Nogo-A was implicated in a range of CNS injuries and diseases. In principle, Nogo-A associated diseases are understood as diseases or trauma of the nervous system associated with nerve and/or vascular repair. Nogo-A inhibition is thought to have a beneficial effect in various diseases of the peripheral (PNS) and central (CNS) nervous system, i.e. more particularly in neurodegenerative diseases such as Alzheimer disease, Parkinson disease, Amyotrophic lateral sclerosis (ALS), Lewy like pathologies or other dementia in general, traumatic brain injury, spinal cord injury, diseases following cranial, cerebral or spinal trauma, stroke or a demyelinating disease. Such demyelinating diseases include, but are not limited to, multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Merzbacher disease, Spongy degeneration, Alexander's disease, Canavan's disease, metachromatic leukodystrophy and Krabbe's disease.

In addition, degenerative ocular disorders can directly or indirectly involve the degeneration of retinal or corneal cells including ischemic retinopathies in general, anterior ischemic optic neuropathy, all forms of optic neuritis, wet and dry age-related macular degeneration (AMD), diabetic retinopathy, diabetic macular edema, cystoid macular edema (CME), retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy, the after effects of corneal transplantation or of refractive corneal surgery, and herpes keratitis. Furthermore, it was shown that Nogo-A can play a role in psychiatric conditions, in particular schizophrenia and depression.

In vivo studies confirmed that treatment with the antibody of the present invention leads to a better recovery of a locomotor tasks requiring fine motor control in a mouse stroke model as shown by irregular horizontal ladder crossing; see Example 11 and FIG. 10.

Hence, the present invention also relates to a method of treating a disease or disorder associated with Nogo-A including those recited above, preferably a disease of the PNS or CNS, which method comprises administering to a subject in need thereof a therapeutically effective amount of any one of the afore-described Nogo-A-binding molecules, antibodies, polynucleotides, vectors or cells of the instant invention. In principle, the anti-Nogo-A antibody of the present invention is suitable for the treatment of the same diseases and disorders disclosed in the references relating to prior anti-Nogo-A antibodies which are cited herein in section "Background of the invention", supra.

In a further embodiment, co-administration or sequential administration of other agents useful for treating a PNS or CNS disease, disorder, or symptoms associated with Nogo-A may be desirable. For example, the antibody, or Nogo-A-binding fragment, variant, or biotechnological derivative thereof of the invention can be administered in combination with anti-inflammatory agents such as but not limited to corticosteroids following stroke or spinal cord injury as a means for blocking further neuronal damage and inhibition of axonal regeneration, neurotrophic factors such as nerve growth factor (NGF), brain-derived neurotropic factor (BDNF) or other drugs for neurodegenerative diseases such as Exelon™ (Rivastigmine) or Levodopa (L-DOPA (3,4-dihydroxy-L-phenylalanine)). Other suitable combination partners for the treatment of stroke are alteplase and desmoteplase (DSPA, e.g., disclosed in WO90/09438). In one embodiment, the present invention provides a combination comprising an antibody or Nogo-A-binding fragment of the invention and desmoteplase, in particular for the treatment of stroke as well as pharmaceutical compositions comprising said combination. As used herein, two agents are said to be administered in combination when the two agents are administered simultaneously or are administered independently in a fashion such that the agents will act at the same time.

The structure of the active ingredients identified by code numbers, generic or trade names may be taken from the actual edition of the standard compendium "The Merck Index" or from databases, e.g. Patents International (e.g. IMS World Publications) or other databases provided by IMS Health.

In another example, cells which express the antibody or Nogo-A-binding fragment, variant, or derivative thereof of the invention may be transplanted to a site of spinal cord injury to facilitate axonal growth throughout the injured site. Such transplanted cells would provide a means for restoring spinal cord function following injury or trauma. Such cells could include olfactory ensheathing cells and stem cells of different lineages of fetal nerve or tissue grafts.

Several documents are cited throughout the text of this specification. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1: Isolation and Identification of
Anti-Nogo-A Antibodies

Human-derived antibodies targeting Nogo-A were identified utilizing the Reverse Translational Medicine™ (RTM™) technology, a proprietary technology platform by Neurimmune AG originally described in the international application WO 2008/081008 but modified, further refined and specifically adapted to the target Nogo-A.

Example 2: Determination of Antibody Sequence
and Recombinant Expression

The amino acid sequences of the variable regions of the above-identified anti-Nogo-A antibodies were determined on the basis of their mRNA and cDNA sequences, respectively, obtained from human memory B cells; see FIG. 1A, B. Recombinant expression of complete human IgG1 antibodies with a human or mouse constant domain was performed substantially as described in the Examples of WO 2008/081008, e.g., as described in the Methods section at page 99 and 100.

The framework and complementarity determining regions were determined by comparison with reference antibody sequences available in databases such as Abysis (www.bio-inf.org.uk), and annotated using the Kabat numbering scheme (www.bioinf.org.uk).

Example 3: Binding Characteristics

The neurite outgrowth inhibitor Nogo-A contains 3 inhibitory regions. Two are shared with the splice variant Nogo-B (Nogo-66 located between the two transmembrane regions and the NIR domain at the tip of the N-terminus) and one is shared with the splice variant Nogo-C(Nogo-66). The unique, highly inhibitory domain for neurite outgrowth of Nogo-A is located in the exon 3 of Nogo-A and is called delta 20 region (d20; human aa position 566-748) (Oertle et al., J. Neurosci. 23 (2003), 5393-5406). To confirm the binding properties of antibodies NG004 NG034 and to monitor for cross-reactivity to other species like rat, an ELISA with a fragment containing the d20 region plus some additional amino acids C- and N-terminal of the inhibitory region (human aa position 543-866) was performed. This fragment is called rat or human d20plus and is recombinantly produced in *E. coli*. To examine that the antibody binds strongly to the d20plus region and to compare the binding properties of the subject antibodies NG004 and NG034 to the already known antibodies (11C7 and Ozanezumab) the ELISA was used and $EC_{50}$ values were compared.

The ELISA is performed according to a standard protocol (Engvall & Perlmann, J. Immunol. 109 (1972), 129-135, Engvall & Perlmann, Immunochemistry 8 (1971), 871-874). In brief, ELISA plates are coated with 3 μg/ml of either rat or human sequence derived d20plus, blocked with 5% milk powder (Rapilait, Migros) and probed with NG004. Each plate contains a serial dilution of 11C7 and/or Ozanezumab as internal standard. Finally the plates are incubated with the corresponding secondary antibodies (11C7 with anti-mouse HRP (Invitrogen, A16078), NG004 and Ozanezumab with anti-human HRP (Sigma, A0170-1ML)). The plates are developed with TMB substrates (ThermoFisher) and stopped with 1M HCl. The readouts are performed on the Tecan Sparc plate reader.

As shown in FIG. 2A, NG004 binds human d20plus region at physiological pH with high affinity in low nM range with an $EC_{50}$ of 0.26 nM. The $EC_{50}$ values of antibody 11C7 are 0.14 nM and 0.20 nM for Ozanezumab. The corresponding rat peptide d20plus is only weakly bound by NG004 (FIG. 2B). These data confirm that the delta20 region is the active binding site within the Nogo-A protein.

As shown in FIGS. 2C and D, NG034 binds both the human and rat d20plus region at physiological pH with high affinity in low nM range with an $EC_{50}$ of 0.298 nM for the human version and 0.229 nM for the rat version.

In addition, it has been shown that NG004 and NG034 positively stain rat corpus callosum oligendrocytes (unfixed) (FIG. 2E), rat corpus callosum spinal cord (fixed) as well as fixed human MO3.13, rat NS-1 cells as well as oligodendrocytes and motoneurons in rat CNS tissue, wherein the staining patterns are similar to those of e.g., Ozanezumab.

Example 4: Assessment of the Binding Epitope of
Antibody NG004

Epitope mapping of NG004 was performed using scans of overlapping peptides. The sequences of the d20plus region of Nogo-A (aa 543-866 of human Nogo-A) were synthesized as linear 15-mer peptides with an 11 amino acid overlap between individual peptides. Those peptides were spotted onto nitrocellulose membranes (JPT Peptide Technologies, Berlin, Germany). The membrane was activated for 5 min in methanol and washed in TBS for 10 min at RT. Non-specific binding sites were blocked for 2 hours at RT with Roti®-Block (Carl Roth GmbH+Co. KG, Karlsruhe, Germany). NG004 (1 µg/ml) was incubated in Roti®-Block for 3 h at room temperature. Binding of primary antibody was determined using HRP-conjugated donkey anti-human IgG secondary antibody. Blots were developed and evaluated using ECL and ImageQuant 350 detection (GE Healthcare, Otelfingen, Switzerland).

Antibody NG004 recognizes the spots 34, 35 and 36 (FIG. 3, white box) which correspond to the sequence 141-IN-AALQE-147 (SEQ ID NO: 21) within the d20plus region of Nogo-A. Furthermore, alanine and truncations scans have been performed confirming the identified minimal epitope.

Example 5: Competition Assay

The assay is based on the method provided by Kwak & Yoon, J. Immunol. Methods 191 (1996), 49-54. In particular, the antigen hu d20+ was coated followed by blocking with 5% milk powder in TBS-0.1% tween20. After blocking, the competitor antibodies 11C7 and Ozanezumab were incubated at the $EC_{50}$ concentration or higher of the particular antibody. After washing, either mouse IgG1 or human IgG4 isotypes of NG004 or NG034 were added to the wells as a serial dilution starting at a concentration of 30 µg/ml (200 nM). A three-fold serial dilution was performed over 12 dilutions. If competition with the competitor antibodies occurs this will lead to a reduced binding of NG004 or NG034, shown as a shift of the $EC_{50}$ value and or a diminishing absorbance value of the high concentration plateau.

NG004 does not show competitive binding to Nogo-A with the antibodies Ozanezumab (FIG. 4A) and 11C7 (FIG. 4B). NG034 does not show competitive binding to Nogo-A with the antibodies 11C7 and NG004 (FIG. 4C).

Example 6: Target Engagement in In Vivo Model

Antibodies were administered to intact, adult rats (Long Evans, Janvier) via osmotic minipumps (Alzet 2ML1 pumps) intrathecally over the lumbar spinal cord for 7 days with a pumping rate of 10 µl/h. After this period, the animals were sacrificed and the tissue was processed to evaluate the effect of the antibodies on biomarkers. In particular, animals were anaesthetized and perfused transcardially with saline followed by 4% formalin. CNS tissue samples were then embedded in OCT mounting medium, frozen and cut on a cryostat. The effect of the infused antibodies NG004.m1, 11C7 (positive control) and isotype control anti-BrdU (AbD Serotec) was tested on selected biomarkers namely Nogo-A, Nogo-B and NgR1.

Statistical analysis has been performed with Prism 7.0 (GraphPad Software Inc.) and R (R version 3.4.1). For statistical tests within groups over time, ordinary one-way ANOVA followed by Dunnett's multiple comparisons test are used. To detect differences between groups and within groups over time and for comparison of more than two groups over time, two-way ANOVA with repeated measures followed by Tukey multiple comparisons test will be used. The threshold for significance for all experiments is set at *P<0.05. Smaller P-values are represented as **P<0.01 and

***P<0.001. In bar graphs, all data are plotted as means±SEM (standard error of the mean). In box plot graphs, data are represented as median±25th percentile (box) and min/max (whiskers). In all graphs, dots represent individual animals.

Figure 5:
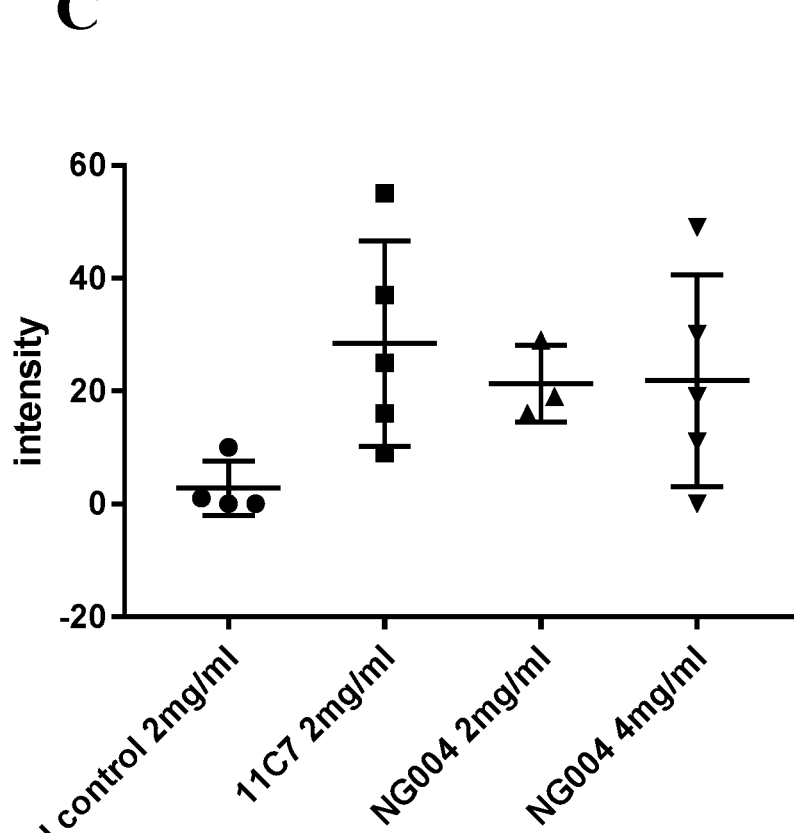
FIG. 5: In vivo target engagement of NG004 was analyzed by intrathecal treatment of rats with NG004 for one week and subsequent analyses of Nogo-A and Nogo-B protein levels in the CNS by immunofluorescence staining. (A) NG004 downregulates endogenous Nogo-A levels in the CNS. (B) NG004 upregulates endogenous Nogo-B levels in the CNS. (C) NG004 upregulates endogenous NgR1 levels in the CNS.

Intrathecal treatment of rats treated with 2 mg and 4 mg NG004, respectively, for one week results in downregulation of endogenous Nogo-A protein levels in the CNS as assessed by immunofluorescence staining (FIG. 5A). Antibody 11C7 was used as positive control. In contrast, NG004 and 11C7 upregulate endogenous Nogo-B protein levels in the CNS (FIG. 5B). The CA3 region of the hippocampus of rats infused for 7 days with anti-Nogo-A antibodies NG004 and 11C7 showed a significant higher fluorescence intensity for NgR1 compared to rats treated with the control, anti-BrdU antibody. Thus, there is a significant upregulation of NgR1 (FIG. 5 C).

Example 7: LTP Assay

It has been shown that Nogo-A neutralization with antibody 11C7 significantly increased long-term synaptic plasticity (long-term potentiation, LTP) in mouse hippocampi (Delekate et al., PNAS 108 (2011), 2569-2574). NG004 has been analyzed for its potency to increase LTP according to the published protocol (Delekate et al. (2011), supra).

As shown FIG. 6B, NG004 demonstrates a similar ex vivo activity as the positive control 11C7 (compare FIGS. 6A and B). In addition, higher doses of NG004 (25 µg/ml) increases the effect size and onset of the action.

Example 8: In Vitro Neurite Outgrowth Assay

In order to assess the biological activity of the anti-Nogo-A antibodies, a neurite outgrowth inhibition assay was performed. When neuronal cells in culture are treated with crude brain and spinal cord detergent extract (Nogo-A containing extract), neurite outgrowth is inhibited. Earlier studies have shown that this inhibitory activity can be neutralized by about 20% by specific antibodies against Nogo-A, e.g. 11C7, ATI355, or Ozanezumab (Oertle et al. (2003), supra; Liebscher et al. (2005), supra; Weinmann et al., Mol. Cell Neurosci. 32 (2006), 161-173). The assay was performed according to a protocol established by Rubin et al., Europ. J. Neurosci. 7 (1995), 2524-2529 with adaptations, wherein it was shown that neurite outgrowth of primary neurons or neuroblastoma cells is inhibited by rat spinal cord extract or non-human primate CNS extract (CNSE) (containing Nogo-A) and the partial reversal/neutralization of this inhibition by functionally active anti-Nogo-A antibodies. The biological activity of NG004 and NG034 was tested in comparison to the positive control anti-Nogo-A antibodies 11C7 and ATI355.

The NIE-115 cell line was established in 1971 by T. Amano, E. Richelson, and M. Nirenberg by cloning the C-1300 spontaneous mouse neuroblastoma tumor. NIE-115 cells were supplied by American Type Culture Collection (ATCC); ordering number: ATCC® CRL-2263. For differentiation, adherent NIE-115 cells are grown in 48 well plates in differentiation medium (Neurobasal® medium supplemented with 2% L-glutamine) The cells were harvested and resuspended in serum-free differentiation medium to obtain a cell suspension density of $2.2 \times 10^4$ cells/ml. Then 450 µl of cell suspension per well were plated to the 48 well plate resulting in final density of $1 \times 10^4$ cells per well and incubated for 24 hours in a humidified incubator under 5% $CO_2$ at 37° C. prior to the addition of the inhibitory extracts and test antibodies.

In order to ensure comparability of independent assays, the half-maximal inhibition ($HMI_{50}$) value of the CNS extract needed to be determined each time a new preparation of CNS extract was performed. The procedure to determine the CNS extract's $HMI_{50}$ value was performed with three wells per concentration as follows: The CNS extract was added with an increasing concentration (5 µg/ml, 10 µg/ml, 12.5 µg/ml, 15 µg/ml 20 µg/ml, 40 µg/ml) to the NIE-115 cells premixed in PBS to a final volume of 50 µl per well. After 24 hours the cells were fixed and Coomassie stained for analysis. The Coomassie stained cells were imaged using a semi-automated IN Cell Analyzer 2500HS, wherein eight 10× bright field images of each well at predefined locations were acquired, four of which were analyzed for the determination of the $HMI_{50}$ value. The $HMI_{50}$ value was estimated by eye based on the morphological criteria: for the solvent control (PBS) approximately 80% of NIE-115 cells show medium-long neurites; the number of neurite-bearing cells is decreased to 60% by, e.g., 12.5 µg/ml CNS extract; the number of neurite-bearing cells is decreased to 40% by, e.g., 20 µg/ml CNS extract; the number of neurite-bearing cells is decreased to almost 0% by, e.g., 40 µg/ml CNS extract. Based on these morphological criteria, the $HMI_{50}$ value can be defined as 50% of the cells that show a neurite-bearing cell morphology in comparison to the solvent control condition. The $HMI_{50}$ value was kept constant for each experiment using the same source of CNS extract. If a new CNS extract was prepared, the $HMI_{50}$ needed to be determined again.

NIE-115 cells were treated with CNS extract and the antibodies to be tested (NG004.h4.ml-backbone human IgG4 S228P; NG004.ml-backbone mouse IgG1) and incubated for another 24 hours before fixation, Coomassie staining and image acquisition. For analyzing the TIFF images a built-in grid plugin and cell counter plugin of Fiji (ImageJ software) was used. Pixels were converted into $\mu m^2$ on the basis of the objective magnification. A counting frame-grid was superimposed onto an image with a fixed area per point size (21'708.8 $\mu m^2$) between its lines. By use of a computer mouse, the cell bodies per image (counter 1) were marked and counted by Fiji Cell Counter software plugin. Likewise, the intersections between neurites (processes longer than cell body diameter) and grid lines (counter 2) were marked. To quantify the neurite outgrowth in a precise way, specific cut-offs were set: (a) cell bodies are not counted when they touch the outer border of the picture frame; (b) processes are considered neurites, when they are longer than the cell body diameter; (c) intersections with the outer border of the counting frame are not counted; (d) dead cells are excluded from counting. What is considered a dead cell was judged visually by round and small morphology (Ronn et al., J. Neurosci. Methods 100 (2000), 25-32). The resulting ratio between the number of intersections and the number of cells was then calculated by following formula: Mean neurite outgrowth per cell=Total number of intersections/total cell number.

For each experimental condition, four images of each of three well replicates/experiment and from three independent experiments were analyzed. Data plotting and statistical analysis was performed with GraphPad Prism 7.03 software. Data were statistically analyzed using the post-hoc one-way ANOVA.

As shown in FIGS. 7A and B, treatment of differentiated, rat CNS extract treated NIE-115 cells with antibody NG004 stimulates neurite outgrowth, i.e. the Nogo-A induced inhibition of neurite outgrowth is reversed. The $IC_{50}$ values of NG004 for this effect are 11.16 nM and 19.34 nM for the positive control antibody 11C7. Furthermore, FIGS. 7C and D show that anti-Nogo-A antibodies NG004 and NG034 demonstrated functional activity similar to the internal reference antibody ATI355 for neurite outgrowth enhancement in presence of growth inhibitory primate CNS extract. Anti-Nogo-A antibodies NG004 and NG034 neutralized the crude non-human primate CNS extract (Nogo-A containing) mediated neurite outgrowth inhibition and demonstrate evidence of biological activity in a species phylogenetically close to humans. The isotype control antibody 3.1 (recombinant human anti-IAV HA antibody Fab fragment mAb 3.1, Wyrzuckia et al., J. Virol. 88 (2014), 7083-7092) was used as negative control and anti-Nogo-A antibody ATI355 as positive control.

Example 9: Angiogenesis in In Vivo Stroke Mouse Model

In addition to its neurite growth inhibition, Nogo-A has also been shown to act as a negative regulator of angiogenesis in the developing the CNS (Wälchli et al., Proc Natl Acad Sci 110 (2013), E1943-52). Accordingly, the potential of a monoclonal anti-Nogo-A antibody, NG004, to increase angiogenesis in the penumbra after stroke injury was investigated in comparison to the previously established anti-Nogo-A antibody 11C7 or control antibody FG12/B5 (Muranova et al., Acta Crystallogr. D. Biol. Crystallogr. 60 (2004), 172-174) in a mouse model of stroke (Rust et al., PNAS 116 (2019), 14270-14279, and Watson et al., Ann. Neurol. 17 (1985), 497-504). Antibodies were administered to stroked, adult mice via osmotic minipumps implanted into the cerebral ventricle for 14 days. After 21 days, the animals were sacrificed and the tissue was processed to evaluate the vascular network in the penumbra and the effect of the antibodies (NG004, 11C7, FG12/B5) on vascular area fraction, number of vascular branches, vascular length and diameter as well as the distance between vessels after stroke. Therefore, adult female mice (10 weeks) received a photo-thrombotic stroke of their right motor cortex according an established protocol (Wahl et al., Science 50 (2014), 1250-1255, and Bachmann et al., J. Neurosci. 34 (2014), 3378-3389). To label proliferating vascular endothelial cells mice received three consecutive i.p. injections of 5-ethynyl-2'-deoxyuridine (EdU, 50 mg/kg body weight, ThermoFisher) on day 6, 7 and 8 after stroke. EdU incorporation was detected 21 days after stroke using the Click-iT EdU Alexa Fluor 647 Imaging Kit (ThermoFisher) on 40 µm free floating coronal sections. For constant CNS delivery, antibodies were filled into osmotic Alzet minipumps model number 1002 (0.25 µl/h pumping rate, Alza Corporation, Palo Alto, USA) with 32 ga catheters (CR3218, ReCathCo, LLC, 2853-106 Oxford Boulevard, Allison Park, PA 15101) and applied into the contralesional cerebral lateral ventricle according to a known protocol (Ineichen et al., Nature Protocols 12 (2017), 104-131). Each animal received one of the osmotic pumps filled with the assigned antibody: IgG1 mouse monoclonal antibody 11C7 (positive control); FG12/B5 (negative control); IgG1 chimeric monoclonal antibody NG004. The concentrations of all antibodies were 7 mg/ml. To assess the general health status, the animals were daily weighed and an interactive neuro-score was recorded according to a previously published protocol (Shelton et al., J. Neurosci. Methods 168 (2008), 431-442). No statistical differences between the groups were observed, although NG004 receiving animals tended to have a better recovery within the first days. After 21 days, animals were sacrificed and perfused transcardially and brain sections obtained according to a standard protocol (Rust et al., Proc. Natl. Acad. Sci. USA 116 (2019), 14270-14279). To assess the effect of the infused antibodies NG004, 11C7 and FG12/B5 on angiogenesis within the penumbra, different biologically relevant vascular parameters were evaluated including vascular area fraction, vascular length, vascular branching, vascular distance and variability of distance. Furthermore, the formation of newly formed vessels was assessed by incorporation of the nucleotide analogue and mitosis marker EdU into nuclei of CD-31-positive vascular endothelial cells as determined following immunohistochemical staining with anti-CD31 antibody (rat, 1:50, BD Biosciences #550274).

Newly generated blood vessels were identified by quantifying the amount of CD31/EdU double-positive cells within the ischemic border zone. Images were analyzed with ImageJ (FIJI). Images were converted into 8-bit format and manually thresholded with the Adaptive Threshold plugin to get a binarized image. A median of 0.5 pixels was applied to remove noise. The region of interest (ROI) was manually selected and analyzed for all parameters; 1) area fraction: The percentage of pixels in ROI that have been highlighted and are not zero; 2) vascular length: The image was skeletonized and analyzed with the plugin Skeleton length tool—the length of all structures in the ROI was summed up; 3) number of branches was assessed by the Analyze Skeleton tool; 4) distance and variability of the vessels was calculated by NND tool that calculated the minimal distance between the single vessels. From this the mean and the standard deviation were calculated to get information about the average distance and variability in distribution between the vessels in ROI. The values vascular length and number of branches was normalized to the total area of the region of interest. Statistical analysis was performed with Prism 7.0 (GraphPad Software Inc.) and R (R version 3.4.1). For statistical tests within groups over time, ordinary one-way ANOVA followed by Dunnett's multiple comparisons test were used. To detect differences between groups and within groups over time and for comparison of more than two groups over time, two-way ANOVA with repeated measures followed by Tukey multiple comparisons test was used. For correlation analysis between behavioral recovery and outsprouting fibers the Spearman correlation was applied. The threshold for significance for all experiments was set at *$P < 0.05$. Smaller P-values are represented as $P < 0.01$ and *$P < 0.001$. In bar graphs, all data are plotted as mean±SEM (standard error of the mean). In box plot graphs, data are represented as median±25th percentile (box) and min/max (whiskers). In all graphs, dots represent individual animals.

Figure 8:
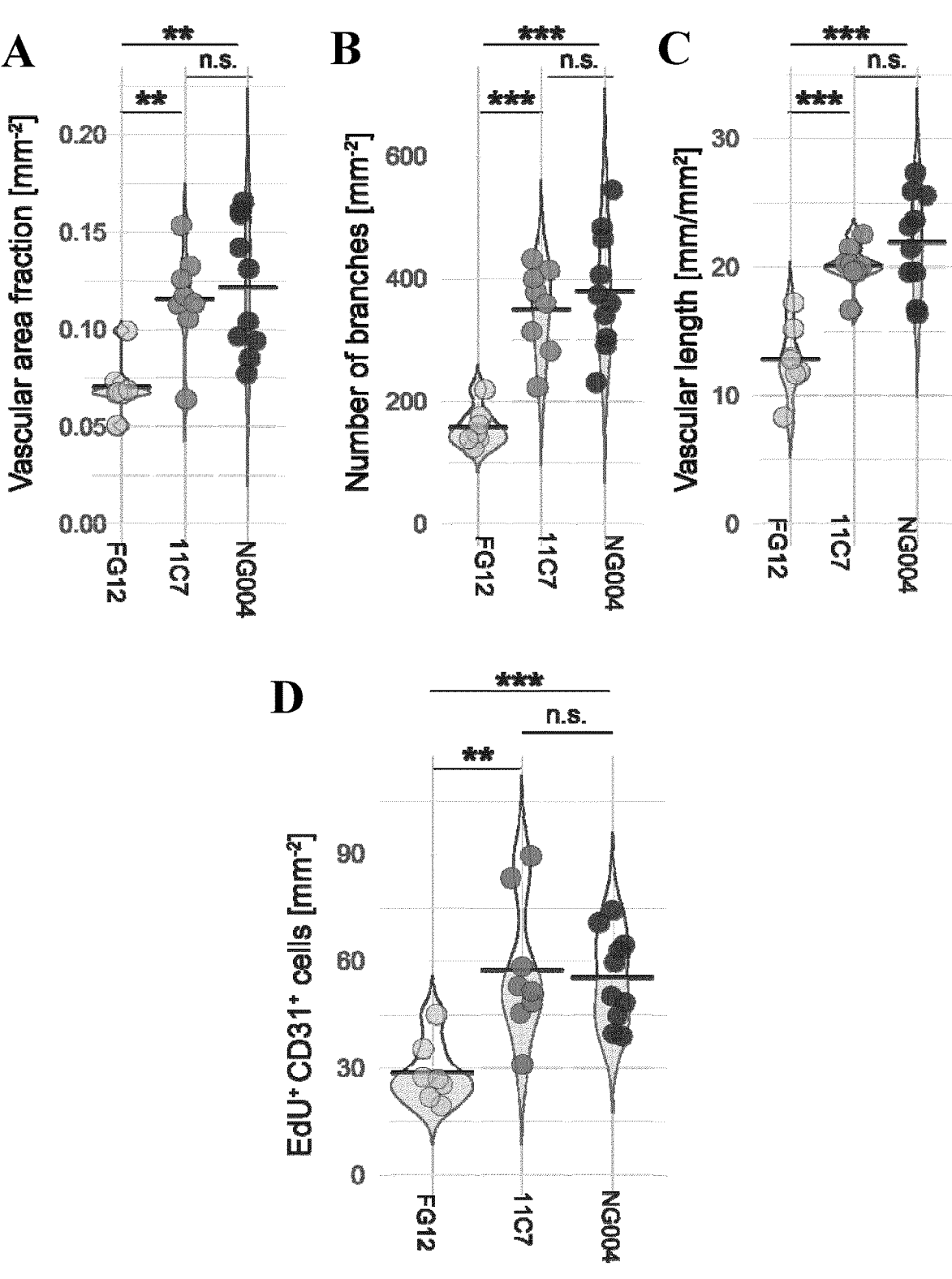
FIG. 8: In vivo stroke model in adult mice; extent of vascular repair in the ischemic border region around the focal stroke core 3 weeks after the stroke. (A) NG004 increases the vascular area within the ischemic border zone compared to control antibody FG12/B5. (B) NG004 increases the number of vascular branches compared to the control antibody FG12/B5. (C) NG004 increases the vascular length within the ischemic border zone compared to the control antibody FG12/B5. (D) NG004 increases the proliferation rate of CD31+ endothelial cells. Effect sizes of all parameters are similar for NG004 and 11C7.

As shown in FIG. 8, stroked brain tissue of NG004 and 11C7 treated animals showed a higher developed vascular bed in the ischemic border zone compared to the controls at 21 days after the stroke. This was shown by increased total area fraction occupied by blood vessels (NG004, 0.12±0.03; 11C7, 0.115±0.03; Ctrl, 0.07±0.01), increased number of branches per mm$^2$ (NG004, 379.18±96.62; 11C7, 349.4±71.96, Ctrl, 156.79±31.82), and the vascular length in mm per mm$^2$ (NG004, 21.90±3.83, 11C7, 20.03±1.69; Ctrl, 12.89±2.82) (FIG. 8A-C) No differences were detected between 11C7 and NG004 in any of the vascular parameters. Importantly, there was no detectable difference in the stroke size between all the groups (data not shown). It was hypothesized that the more highly developed vascular beds in the ischemic border zone are generated through newly formed blood vessels. Therefore, the nucleotide analogue EdU (50 mg/kg body weight) was systemically injected daily at 6-8 days following injury at the peak of angiogenesis. Newly formed vascular endothelial cells (CD31+) were counted in the ischemic border zone. An increased number of CD31/EdU+ cells per mm$^2$ in both groups receiving anti-Nogo-A antibodies (NG004: 55.20±12.7, 11C7: 57.30±19.57) was observed compared to the control (28.51±8.8) (FIG. 8D). In summary, it has been shown that vascular repair is enhanced in both groups treated with anti-Nogo-A antibody to an indistinguishable extent, compared to the control antibody receiving animals three weeks following injury. It has also been shown that the number of newly formed vascular endothelial cells is increased in both groups, the NG004 and the 11C7 treated animals, to the same extent groups. Accordingly, NG004 is a potent anti-Nogo-A antibody for vascular repair following stroke.

Example 10: Antibody Integrity and Stability

For analyzing the antibody's stability and integrity size exclusion chromatography (SEC) was performed according to a standard protocol (Porath & Flodin, Nature 183 (1959), 1657-1659). In brief, antibodies were dialyzed into the different buffers. After dialysis the antibodies were transferred into test tubes and incubated at 40 and 4° C. for up to 9 weeks. At week 1, 2, 4 and 9 samples were pulled and injected into a 100 μl loop from Amersham of a Superdex™ 200 Increase column with a flow rate 0.75 ml/min; as running buffer Dulbecco's PBS at pH7.4 was used.

As shown in FIGS. 9A and B, antibody NG004 is highly stable at different pH values (pH 6, 7.4, 8) and in artificial CSF as well as after repeated freeze-thaw cycles. Furthermore, no degradation and aggregation was observed and avidity was maintained (data not shown).

Example 11: Functional Recovery of Locomotor Task after Treatment with NG004

The preclinical efficacy of the human NG004 monoclonal anti-Nogo-A antibody in comparison to the previously established anti-Nogo-A antibody 11C7 or control antibody ("anti-BrdU") on motor function recovery, in particular on functional recovery of skilled forelimb function after intrathecal application in a rat model of unilateral photothrombotic stroke was evaluated.

To address functional recovery, well acclimatized and handled young-adult female Long-Evans rats were trained in fine motor behavioral tasks (horizontal ladder test) and their baseline behavioral performance was recorded in three sessions. A photothrombotic stroke directed to the sensory-motor cortex was then applied, and antibodies (11C7; NG004 (IgG1 chimeric monoclonal antibody NG004); anti-BrdU) were administered intrathecally to the stroked rats via osmotic pumps for 14 days. The behavioral performance of the animals was recorded after stroke induction (4 days post injury (dpi)) as well as weekly for up to 9 weeks (7, 14, 21, 28, 35, 42, 49, 56 and 63 dpi).

40 rats were divided into the following groups:
1. NG004_4 mg: 10 rats received a cumulative dose of 4 mg of NG004 over 14 days;
2. NG004_8 mg: 10 rats received a cumulative dose of 8 mg of NG004 over 14 days;
3. 11C7: 10 rats received a cumulative dose of 4 mg of 11C7 over 14 days of (positive control);

4. Anti-BrdU: 10 rats received a cumulative dose of 4 mg of a murine monoclonal antibody against BrdU over 14 days (negative control), wherein four animals had to be sacrificed (two animals from group 1 and each one animal from groups 2 and 4).

Animals were housed in individually ventilated cages (Type IV) in groups of three under a constant 12 h dark/light cycle with food and water ad libitum. Upon arrival from the commercial vendor (Janvier. Labs, Le Genest-Saint-Isle, France), the 40 female Long Evans rats (age: 12-16 weeks, weight: 200-250 g) were acclimated to the animal facility for one week. Afterwards, the experimenters handled the animals according to a standard procedure for one week prior to the start of the experiments to reduce stress levels.

The irregular horizontal ladder walking test is a motor and coordination test for evaluating skilled walking, where specific forepaw placement on the irregularly spaced ladder rungs is judged; see Maier et al., J Neurosci. 28 (2008), 9386-403. The horizontal ladder walking test apparatus consists of side walls made of clear Plexiglas and metal rungs (3 mm diameter), which can be inserted to create a ladder runway with a minimum distance of 1 cm between rungs and a total length of 1 m. The rungs are spaced irregularly to evoke cortical reassessment of step placement with a maximum distance of 3 cm. The baseline horizontal ladder performance was recorded on three consecutive days. Three runs were recorded for each session and were analyzed for paw placement on the rung on high speed video recordings of all the runs.

All animals received a unilateral photothrombotic stroke to lesion the sensorimotor cortex of their preferred paw as previously described in Lindau et al., Brain 137 (2014), 739-756 and Watson et al., Annals of Neurology 17 (1985), 497-504. The animals recovered well from their injury. The affected forelimb showed signs of plegia, but the animals were able to walk, climb, eat and groom themselves. For constant CNS delivery, antibodies were delivered by prepared osmotic pumps filled with the assigned antibody with catheters into the lumbar liquor space right after the photothrombotic stroke surgery. After 14 days the pumps were removed and the behavioral testing started. For the analysis of the horizontal ladder data the success rate for correct forelimb/paw placement was calculated as percent of total steps made by the corresponding limb.

Statistical analysis was performed with Prism 7.0 (GraphPad Software Inc.). For statistical tests within groups over time, two-way ANOVA followed by LSD (Least significant difference) Fisher's test was used. To detect differences between groups at a specific time point, an unpaired onetailed t-test was used. For correlation analysis between behavioral recovery and CST cervical spinal cord sprouting, the Spearman correlation was applied. The threshold for significance for all experiments was set at $*P<0.05$. Smaller P-values are represented as $P<0.01$ and $*P<0.001$. In bar graphs, all data are plotted as means±SEM (standard error of the mean). In all graphs, dots represent individual animals.

Anti-Nogo-A treated animals showed an improved functional recovery in the horizontal ladder task when compared to control antibody treated animals.

At day 4 post injury all animals showed a comparable drop in success rate (for anti-BrdU: a drop to 34.43%±8.08%, for anti-Nogo-A treatment 11C7: a drop to 38.37%±4.87%, for NG004 4 mg/ml a drop to 34.85%±6.12%, and for NG004 8 mg/ml a drop to 33.75%±5.25%). From day 14 onward, the performance of the anti-Nogo-A antibody NG004 8 mg/ml and the 11C7 treated animals constantly improved and reached a significant difference on day 63 post injury when compared to anti-BrdU treated animals; see FIG. 10. Thus, the results showed that anti-Nogo-A antibody NG004 treatment leads to a better recovery of a locomotor task requiring fine motor control as shown by irregular horizontal ladder crossing.

Example 12: Anti-Nogo-A Antibody NG004 has a Reduced Complement-Dependent CDC A C1q binding ELISA assay was performed to analyze Fc characteristics regarding complement-dependent cytotoxicity (CDC) activity of the anti-Nogo-A antibodies, where the deposition of human C1q (Sigma C1740-5 mg) was measured. The C1q deposition was assessed on a 1 µg/ml antibody coated polystyrene plate incubated with eight different concentration of C1q (1.2 to 20 µg/ml) in TBS-0.1% v/v Tween20 0.15 mM $CaCl_2$) and 1 mM $MgCl_2$ for 1 h at 37° C. For the detection, a sheep anti human C1q polyclonal antibody (biorad 2221-5004P) was used. As controls two clinical antibodies with known mechanism of action were used. Rituximab (human IgG1) served as positive and Natalizumab (human IgG4) as negative control. The internal positive control of NG004 IgG4 S228P was NG004 in an IgG1 isotype. After 10 min, the colorimetric TMB reaction was stopped with 1 M HCl and OD at 450 nm was measured on TECAN Spark plate reader.

Figure 11:
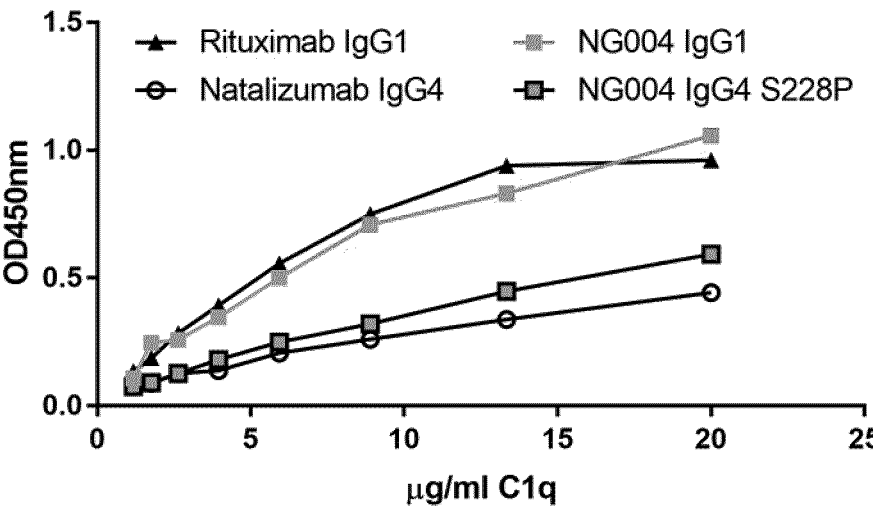
FIG. 11: NG004 isotypes (IgG1 and IgG4), Rituximab (IgG1, Mabtera) and Natalizumab (IgG4, Tysibra) were used to compare C1q binding in an ELISA based CDC assay. NG004 IgG4 S228P shows a reduced reactivity to C1q and behaves similar to other IgG4 (Natalizumab).

NG004 IgG4 S228P anti-Nogo-A antibody and Natalizumab displayed reduced C1q binding activity compared to IgG1 isotypes; see FIG. 11. These results show that NG004 IgG4 S228P behaves similar like other IgG4 and has a reduced CDC.

---

The invention claimed is:

1. A recombinant monoclonal anti-Nogo-A antibody or an antigen-binding fragment thereof, comprising a variable heavy chain (VH) and a variable light chain (VL), wherein (a) the VH comprises a VH complementary determining region 1 (VH-CDR1) comprising the amino acid sequence of SEQ ID NO: 3, a VH complementary determining region 2 (VH-CDR2) comprising the amino acid sequence of SEQ ID NO: 4, and a VH complementary determining region 3 (VH-CDR3) comprising the amino acid sequence of SEQ ID NO: 5; and (b) the VL comprises a VL complementary determining region 1 (VL-CDR1) comprising the amino acid sequence of SEQ ID NO: 8, a VL complementary determining region 2 (VL-CDR2) comprising the amino acid sequence of SEQ ID NO: 9, and a VL complementary determining region 3 (VL-CDR3) comprising the amino acid sequence of SEQ ID NO: 10.

2. The antibody or antigen-binding fragment thereof of claim 1, wherein the VH comprises the amino acid sequence of SEQ ID NO: 2, and the VL comprises the amino acid sequence of SEQ ID NO: 7.

3. The antibody or antigen-binding fragment thereof of claim 1, further comprising an immunoglobulin heavy chain constant region and an immunoglobulin light chain constant region.

4. The antibody or antigen-binding fragment thereof of claim 3, comprising a mutated Fc region with reduced effector functions as compared to a wildtype IgG Fc region.

5. The antibody or antigen-binding fragment thereof of claim 3, wherein the immunoglobulin heavy chain constant region is of IgG type.

6. The antibody or antigen-binding fragment thereof of claim 5, wherein the immunoglobulin heavy chain constant region is of IgG4 type.

7. The antibody or antigen-binding fragment thereof of claim 6, wherein the immunoglobulin heavy chain constant region comprises an S228P mutation, numbered according to the Kabat numbering system.

8. The antibody or antigen-binding fragment thereof of claim 1, wherein the antibody is a human-derived antibody.

9. The antibody or antigen-binding fragment thereof of claim 1, wherein the antigen-binding fragment thereof is selected from the group consisting of a single chain Fv fragment (scFv), an F(ab') fragment, an F(ab) fragment, an F(ab')$_2$ fragment, an Fd, an Fv, a single-chain antibody, and a disulfide-linked Fv (sdFv); and/or the antibody is a chimeric murine-human antibody.

10. The antibody or antigen-binding fragment thereof of claim 1, wherein the antibody or antigen-binding fragment thereof (i) is detectably labeled with a label selected from the group consisting of an enzyme, a radioisotope, a fluorescent compound, a chemiluminescent compound, a bioluminescent compound, a tag, a flag, or a heavy metal;

(ii) is conjugated to polyethylene glycol.

11. The anti-Nogo-A antibody or an antigen-binding fragment thereof of claim 1, wherein the anti-Nogo-A antibody or antigen-binding fragment is produced by a method comprising (a) culturing an isolated host cell comprising one or more polynucleotide(s) encoding the antibody or antigen-binding fragment thereof of claim 1 in a culture medium; and (b) isolating the antibody or antigen-binding fragment thereof expressed by the host cell from the culture medium.

12. The antibody or antigen-binding fragment thereof of claim 11, wherein the antibody or antigen-binding fragment thereof (i) is detectably labeled with a label selected from the group consisting of an enzyme, a radioisotope, a fluorescent compound, a chemiluminescent compound, a bioluminescent compound, a tag, a flag, or a heavy metal;

or (ii) is conjugated to polyethylene glycol.

13. A pharmaceutical composition comprising the antibody or antigen-binding fragment thereof of claim 1 and a pharmaceutically acceptable carrier.

14. A diagnostic kit comprising the antibody or antigen-binding fragment thereof of claim 1.

15. A method for promoting neurite outgrowth, vascular repair and/or motor functional recovery in an injury of the peripheral nervous system (PNS) and/or central nervous system (CNS) in a subject in need thereof, comprising administering the antibody or antigen-binding fragment thereof of claim 1 to the subject.

16. The method of claim 15, wherein the injury of the PNS and/or CNS is cranial trauma, cerebral trauma, spinal trauma, stroke, traumatic brain injury, or a demyelinating disease.

17. The method of claim 15, wherein the injury is spinal cord injury.

18. A method for in vivo detection of Nogo-A in a subject, comprising administering the detectably labeled antibody or antigen-binding fragment thereof of claim 10 to the subject; and detecting presence of an immunocomplex of the detectably labeled antibody or antigen-binding fragment thereof and Nogo-A in vivo by immunofluorescent imaging.

* * * * *